United States Patent [19]
Hattori et al.

[11] Patent Number: 6,114,520
[45] Date of Patent: Sep. 5, 2000

[54] 5'-DEOXY-CYTIDINE DERIVATIVES

[75] Inventors: Kazuo Hattori, Chigasaki; Tohru Ishikawa, Kanagawa-ken; Hideo Ishitsuka, Yokohama; Yasunori Kohchi, Fujisawa; Nobuhiro Oikawa, Yokohama; Nobuo Shimma, Chigasaki; Hitomi Suda, Fujisawa, all of Japan

[73] Assignee: Hoffmann-La Roche Inc., Nutley, N.J.

[21] Appl. No.: 09/484,174

[22] Filed: Jan. 14, 2000

Related U.S. Application Data

[63] Continuation of application No. 09/088,668, Jun. 2, 1998.

[30] Foreign Application Priority Data

Jun. 2, 1997 [EP] European Pat. Off. .............. 97108791

[51] Int. Cl.[7] .......................... C07H 19/06; C07H 19/067
[52] U.S. Cl. .................. 536/28.5; 536/28.51; 536/28.52; 514/49
[58] Field of Search ................................ 536/28.5, 28.51, 536/28.52; 514/49

[56] References Cited

U.S. PATENT DOCUMENTS

| | | | |
|---|---|---|---|
| 4,071,680 | 1/1978 | Cook ..................................... | 536/28.52 |
| 4,328,229 | 5/1982 | Fuji et al. ................................ | 514/274 |
| 4,395,406 | 7/1983 | Gacek et al. ............................. | 514/49 |
| 4,966,891 | 10/1990 | Fuji et al. ................................ | 514/49 |
| 5,472,949 | 12/1995 | Arasaki et al. ........................... | 514/49 |
| 5,476,932 | 12/1995 | Brinkman et al. ...................... | 536/55.3 |
| 5,525,603 | 6/1996 | Shirasaka et al. ....................... | 514/241 |
| 5,736,531 | 4/1998 | Von Borstel et al. .................... | 514/50 |

FOREIGN PATENT DOCUMENTS

| | | |
|---|---|---|
| 204212 | 11/1982 | Czech Rep. . |
| 0316704 | 5/1989 | European Pat. Off. . |
| 0602454 | 6/1994 | European Pat. Off. . |
| 0602478 | 6/1994 | European Pat. Off. . |
| 4123520 | 1/1993 | Germany . |
| 49-116081 | 11/1974 | Japan . |
| 56-077226 | 6/1981 | Japan . |
| 633810 | 12/1982 | Switzerland . |
| 8501871 | 5/1985 | WIPO . |
| 9204901 | 4/1992 | WIPO . |
| 9426761 | 11/1994 | WIPO . |
| 9507917 | 3/1995 | WIPO . |
| 9637214 | 11/1996 | WIPO . |

OTHER PUBLICATIONS

Kim et al., "Stereospezifische Syntheses des Carcerostatikums 5'–Deoxy–5–fluor–uridine (5–DFUR) und Seiner 5'–Deuterierten Derivate," *Helvetica Chim Acta*, 65(5), 1523–1537 (1982).

Perman et al., "Synthesis of 1–(2–Deoxy–β–D–erythro–pentofuranosyl)–5–ethynyl–1,2,3,4–tetrahydropyrimidine–2,4–dione (5'–Ethynyl–2'–deoxyurdines)," *Tetrahedron Letters*, (Issue No. 28), 2427–2430 (1976).

Farina et al., "Palladium–Catalyzed Approach to 5–Substituted Uracil and Uridine Derivatives," *Synlett*, 157–159 (Mar., 1991).

Naguib et al., "Structure–Activity Relationship of Ligands of Dihydrouracil Dehydrogenase from Mouse Liver," *Biochemical Pharmacology*, 38(9), 1471–1480 (1989).

Jones et al., "Synthesis of 5–Ethynylcytosine and 5–Ethynylcytidine," *Tetrahedron Letters*, (Issue No. 28), 2459–2460 (1977).

Nio et al., "A Comparative Study of the Antitumor Activities of 5'–Deoxy–5–fluorouridine and Its Prodrug Trimethoxybenzoyl–5'–deoxy–5–fluorocytidine (Ro09–1390) on Human Digestive Organ Cancer Xenograft Lines Transplanted into Nude Mice," *Anti–Cancer Drugs*, 3(4), 387–393 (1992).

Ishikawa et al., "Antitumor Activities of a Novel Fluoropyrimidine, $N^4$–Pentyloxycarbonyl–5'–deoxy–5–fluorocytidine (Capecitabine)," *Biological and Pharmaceutical Bulletin*, 21(7), 713–717 (Jul., 1998).

(List continued on next page.)

*Primary Examiner*—Gary Geist
*Assistant Examiner*—L Crane
*Attorney, Agent, or Firm*—George W. Johnston; Patricia S. Rocha-Tramaloni; Robert A. Silverman

[57] ABSTRACT

Novel 5'-deoxy-cytidine derivatives represented by the general formula (I)

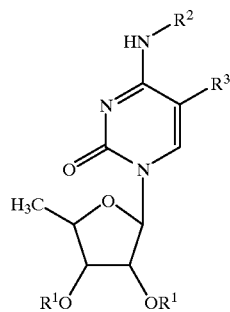

(I)

wherein $R^1$ is a hydrogen atom or a group easily hydrolyzable under physiological conditions; $R^2$ is a hydrogen atom, or —CO—$OR^4$ group [wherein $R^4$ is a saturated or unsaturated, straight or branched hydrocarbon group consisting of one to fifteen carbon atoms, or a group of the formula —$(CH_2)_n$—Y (in which Y is cyclohexyl or phenyl; n is an integer from 0 to 4)]; $R^3$ is a hydrogen atom, bromo, iodo, cyano, a $C_{1-4}$ alkyl group [which may be substituted with halogen atom(s)], a vinyl or ethynyl group [which may be substituted with halogen atom(s), $C_{1-4}$ alkyl, cycloalkyl, aralkyl, or aromatic ring which may have one or more hetero atom(s)], or an aralkyl group which may be substituted for use in medical therapy, especially tumor therapy.

73 Claims, No Drawings

OTHER PUBLICATIONS

Scarano et al., "Enzymatic Deamination of 5'-Deoxycytidylic Acid and 5-Methyl-5'-deoxycytidylic Acid in a Developing Sea Urchin Embryo," *Exptl. Cell Research*, 18, 333–346 (1959); *Chem. Abstr.*, 55(8), Abstr. No. 7681i, (Apr. 17, 1861); only Abstract supplied.

Talarico et al., "Enzymatic Deamination of 5'-Deoxycytidylic Acid in the Embryonic Chick Tissue," *Bull. Soc. Ital. Sper.*, 36, 1056–1058 (1980); *Chem. Abstr.*, 63(11), Abstr. No. 11730c (May 27, 1963); only Abstract supplied.

Theilheimer, *Synthetic Methods of Organic Chemistry*, vol. 7, S. Karger AG, Basel, Switzerland, 1953, only p. 16 supplied.

Krecmerova et al.(I), "Synthesis of 5-Phenylcytosine Nucleoside Derivatives," *Collection of Czech. Chemical Communications*, 61(4), 645–655 (1966).

Krecmerova et al.(II), "Preparation of 5-Benzyluracil and 5-Benzylcytosine Nucleosides as Potential Inhibitors of Uridine Phosphorylase," *Collection of Czech. Chemical Communications*, 61(4), 627–644 (1966).

Hrebabecky et al., "Reaction of Nucleosides with Thionyl Chloride; Preparation of the Deoxy Derivatives of Cytosine and Adenosine," *Collection of Czech. Chemical Communications*, 45(2), 599–605 (1980).

5'-DEOXY-CYTIDINE DERIVATIVES

This is a continuation of copending application Ser. No. 09/088,668, filed on Jun. 2, 1998.

FIELD OF THE INVENTION

The present invention is concerned with novel 5'-deoxy-cytidine derivatives, pharmaceutical compositions, a kit thereof for assisting a delivery of 5-fluorouracil selectively to tumor tissues and process for manufacturing the novel 5'-deoxy-cytidine derivatives.

BACKGROUND

Although 5-fluorouracil (5-FU) or its derivatives are clinically useful antitumor agents for the treatment of various solid tumors, in general they are still not satisfactory in terms of efficacy and safety. These drawbacks are mainly due to rapid inactivation of 5-FU by dihydropyrimidine dehydrogenase (DPD) and/or the unsatisfactory delivery of 5-FU to tumor tissues with respect to tumor selectivity. The attempts to enhance the antitumor activity of 5-FU or its derivatives by inhibition of DPD have already been reported : the co-administration of 5-FU or its derivative with a DPD inhibitor such as uracil [U.S. Pat. No. 4,328,229], 5-ethynyluracil [WO92/04901], 5-chloro-2,4-dihydroxypyridine [U.S. Pat. No. 5,525,603] etc. Such co-administration resulted in enhancement of the antitumor activity of 5-FU or its derivatives, but the safety profile was not so improved due to insufficient selectivity in delivering the DPD inhibitor to tumor tissues (as a consequence, 5-FU level is increased both in tumor and plasma).

SUMMARY OF THE INVENTION

The present invention relates to 5'-deoxy-cytidine derivatives of the formula (I),

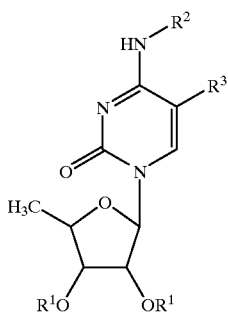

(I)

wherein $R^1$ is a hydrogen atom or a group easily hydrolyzable under physiological conditions; $R^2$ is a hydrogen atom, or —CO—$OR^4$ group [wherein $R^4$ is a saturated or unsaturated, straight or branched hydrocarbon group consisting of one to fifteen carbon atoms, or a group of the formula —$(CH_2)_n$—Y (in which Y is cyclohexyl or phenyl; n is an integer from 0 to 4)]; $R^3$ is a hydrogen atom, bromo, iodo, cyano, a $C_{1-4}$ alkyl group [which may be substituted with halogen atom(s)], a vinyl or ethynyl group [which may be substituted with halogen atom(s), $C_{1-4}$ alkyl, cycloalkyl, aralkyl, or aromatic ring which may have one or more hetero atom(s)], or an aralkyl group which may be substituted; with the proviso that $R^2$ and $R^3$ do not simultaneously mean a hydrogen atom.

The present invention also relates to pharmaceutical compositions comprising a 5'-deoxy-cytidine derivative of formula (I) and a pharmaceutically acceptable inert carrier material.

In accordance with the present invention it has been found that the co-administration of a 5'-deoxy-cytidine derivative of the formula (I) with 5-FU or its derivative results in the significantly improved delivery of 5-FU selectively to tumor tissues as compared with the combination of 5-FU or its derivative with a known DPD inhibitor such as 5-ethynyluracil, and shows significantly improved antitumor activity in human cancer xenograft models.

The present invention also relates to pharmaceutical compositions comprising a 5'-deoxy-cytidine derivative of formula (I) and 5'-fluorouracil or a derivative thereof.

DETAILED DESCRIPTION OF THE INVENTION

The respective groups of the formula (I) are explained in more detail as follows;

Explanation of $R^1$:

$R^1$ is a hydrogen atom or a group easily hydrolyzable under physiological condition.

In the above, the term "a group easily hydrolyzable under physiological condition" preferably means acetyl, propionyl, benzoyl, toluoyl, glycyl, alanyl, β-alanyl, valyl, lysyl, and the like. In the most preferred embodiment of the compounds in accordance with the present invention, $R^1$ means hydrogen, or acetyl.

Explanation of $R^2$:

$R^2$ is a hydrogen atom, or —CO—$OR^4$ group [wherein $R^4$ is a saturated or unsaturated, straight or branched hydrocarbon group consisting of one to fifteen carbon atoms, or group of formula —$(CH_2)_n$—Y (in which Y is cyclohexyl or phenyl; n is an integer of from 0 to 4)].

In the above group $R^4$, the term "a saturated or unsaturated, straight or branched hydrocarbon group consisting of one to fifteen carbon atoms" preferably means methyl, ethyl, n-propyl, 1-isopropyl-2-methylpropyl, 1,1,2-trimethylpropyl, n-butyl, isobutyl, 2-ethylbutyl, 3,3-dimethylbutyl, n-pentyl, isopentyl, neopentyl, 2-propylpentyl, n-hexyl, 2-ethylhexyl, n-heptyl, n-octyl, allyl, 2-buten-1-yl, 3-buten-1-yl, 3-penten-1-yl, 4-penten-1-yl, 3-hexen-1-yl, 4-hexen-1-yl, 5-hexen-1-yl, n-tridecyl and the like.

The term "a group of the formula —$(CH_2)_n$—Y (in which Y is cyclohexyl or phenyl; n is an integer from 0 to 4)" preferably means cyclohexyl, cyclohexylmethyl, 2-cyclohexylethyl, 3-cyclohexylpropyl, 4-cyclohexyl-butyl, phenyl, benzyl, phenethyl, 3-phenylpropyl, 4-phenylbutyl and the like.

In the most preferred embodiment of the compounds in accordance with the present invention, $R^4$ means n-propyl, n-butyl, n-pentyl, isopentyl, neopentyl, n-hexyl, 3,3-dimethylbutyl, 2-ethylbutyl, phenylethyl, and cyclohexylmethyl.

Explanation of $R^3$:

$R^3$ is a hydrogen atom, bromo, iodo, cyano, a $C_{1-4}$ alkyl group [which is unsubstituted or substituted with one or more halogen atom(s)], a vinyl or ethynyl group [which is unsubstituted or substituted with one or more halogen atom (s), $C_{1-4}$ alkyl, cycloalkyl, aralkyl, or aromatic ring which may have one or more hetero atom(s)], or an aralkyl group which is unsubstituted or substituted; with the proviso that $R^2$ and $R^3$ do not mean a hydrogen atom at the same time.

In the above, the term "a $C_{1-4}$ alkyl group which is unsubstituted or substituted with one or more halogen atom (s)" preferably means methyl, trifluoromethyl, ethyl, propyl and the like.

The term "a vinyl or ethynyl group [which is unsubstituted or substituted with one or more halogen atom(s), $C_{1-4}$ alkyl, cycloalkyl, aralkyl, or aromatic ring which may have one or more hetero atom(s)]" preferably means vinyl, 1-chlorovinyl, 2-bromovinyl, 2-bromo-1-chlorovinyl, ethynyl, prop-1-ynyl, but-1-ynyl, pent-1 -ynyl, hex-1 -ynyl, 3,3-dimethyl-but-1 -ynyl, cyclopentylethynyl, cyclohexylethynyl, phenylethynyl, 3-phenylprop-1-ynyl, pyrid-2-ylethynyl, imidazol-2-ylethynyl, and the like. The most preferred group is ethynyl, vinyl and iodo.

The term "an aralkyl group which is unsubstituted or substituted" preferably means 3-(benzyloxy)benzyl, 3-methoxybenzyl, 3-bromobenzyl, 3-methylbenzyl, 3-hydroxybenzyl and the like.

Preferred 5'-deoxy-cytidine derivatives of the present invention are:

5'-deoxy-5-ethynylcytidine,
5'-deoxy-5-prop-1-ynylcytidine,
5-but-1-ynyl-5'-deoxycytidine,
5'-deoxy-5-pent-1-ynylcytidine,
5'-deoxy-5-hex-1-ynylcytidine,
5'-deoxy-5-iodocytidine,
5-bromo-5'-deoxycytidine,
5-(1-chlorovinyl)-5'-deoxycytidine,
5'-deoxy-5-vinylcytidine,
5'-deoxy-5-trifluoromethylcytidine
5-(3-benzyloxybenzyl)-5'-deoxycytidine,
5-cyano-5'-deoxycytidine,
5'-deoxy-N$^4$-(n-pentyloxycarbonyl)cytidine,
5'-deoxy-N$^4$-(n-pentyloxycarbonyl)-5-prop-1-ynylcytidine,
5-but-1-ynyl-5'-deoxy-N$^4$-(n-pentyloxycarbonyl)cytidine,
5'-deoxy-5-pent-1-ynyl-N$^4$-(n-pentyloxycarbonyl)cytidine,
5'-deoxy-5-hex-1-ynyl-N$^4$-(n-pentyloxycarbonyl)cytidine,
5'-deoxy-5-iodo-N$^4$-(n-pentyloxycarbonyl)cytidine,
5-bromo-5'-deoxy-N$^4$-(n-pentyloxycarbonyl)cytidine,
5-(1-chlorovinyl)-5'-deoxy-N$^4$-(n-pentyloxycarbonyl)cytidine,
N$^4$-(ethoxycarbonyl)-5'-deoxy-5-vinylcytidine,
5'-deoxy-N$^4$-(n-propoxycarbonyl)-5-vinylcytidine,
N$^4$-(n-butoxycarbonyl)-5'-deoxy-5-vinylcytidine,
5'-deoxy-N$^4$-(n-pentyloxycarbonyl)-5-vinylcytidine,
N$^4$-(benzyloxycarbonyl)-5'-deoxy-5-vinylcytidine,
5'-deoxy-N$^4$-(n-pentyloxycarbonyl)-5-trifluoromethylcytidine,
5-(3-benzyloxybenzyl)-5'-deoxy-N$^4$-(n-pentyloxycarbonyl)cytidine,
5-cyano-5'-deoxy-N$^4$-(n-pentyloxycarbonyl)cytidine,
5'-deoxy-5-ethynyl-N$^4$-(methoxycarbonyl)cytidine
5'-deoxy-N$^4$-(ethoxycarbonyl)-5-ethynylcytidine
5'-deoxy-5-ethynyl-N$^4$-(n-propoxycarbonyl)cytidine,
5'-deoxy-5-ethynyl-N$^4$-(isopropoxycarbonyl)cytidine,
N$^4$-(n-butoxycarbonyl)-5'-deoxy-5-ethynylcytidine,
5'-deoxy-5-ethynyl-N$^4$-(isobutoxycarbonyl)cytidine,
5'-deoxy-5-ethynyl-N$^4$-(n-pentyloxycarbonyl)cytidine,
5'-deoxy-5-ethynyl-N$^4$-[(2-propylpentyloxy)carbonyl]cytidine,
5'-deoxy-5-ethynyl-N$^4$-(isopentyloxycarbonyl)cytidine,
5'-deoxy-5-ethynyl-N$^4$-[(2-methylpentyloxy)carbonyl]cytidine,
5'-deoxy-5-ethynyl-N$^4$-[(3-methylpentyloxy)carbonyl]cytidine,
5'-deoxy-5-ethynyl-N$^4$-(n-hexyloxycarbonyl)cytidine,
5'-deoxy-N$^4$-[(2-ethylbutyl)oxycarbonyl]-5-ethynylcytidine,
5'-deoxy-N$^4$-[(2-ethylhexyl)oxycarbonyl]-5-ethynylcytidine,
5'-deoxy-5-ethynyl-N$^4$-[(2-phenylethoxy)carbonyl]cytidine,
N$^4$-(cyclohexyloxycarbonyl)-5'-deoxy-5-ethynylcytidine,
N$^4$-[(cyclohexylmethoxy)carbonyl]-5'-deoxy-5-ethynylcytidine,
5'-deoxy-5-ethynyl-N$^4$-(neopentyloxycarbonyl)cytidine,
5'-deoxy-N$^4$-[(3,3-dimethylbutoxy)carbonyl]-5-ethynylcytidine,
2',3'-di-O-acetyl-5'-deoxy-5-ethynyl-N$^4$-(n-propoxycarbonyl)cytidine
2',3'-di-O-acetyl-5'-deoxy-5-ethynyl-N$^4$-(n-pentyloxycarbonyl)cytidine
2',3'-di-O-acetyl-5'-deoxy-5-vinylcytidine,
2',3'-di-O-acetyl-N$^4$-(ethoxycarbonyl)-5'-deoxy-5-vinylcytidine
2',3'-di-O-acetyl-5'-deoxy-N$^4$-(n-propoxycarbonyl)-5-vinylcytidine,
2',3'-di-O-acetyl-N$^4$-(n-butoxycarbonyl)-5'-deoxy-5-vinylcytidine,
2',3'-di-O-acetyl-5'-deoxy-N$^4$-(n-pentyloxycarbonyl)-5-vinylcytidine,
2',3'-di-O-acetyl-N$^4$-(benzyloxycarbonyl)-5'-deoxy-5-vinylcytidine.
5'-deoxy-5-ethynyl-N$^4$-(n-decyloxycarbonyl)cytidine
5'-deoxy-5-ethynyl-N$^4$-[(2,6-dimethylcyclohexyloxy)carbonyl]cytidine
5'-deoxy-5-ethynyl-N$^4$-(benzyloxycarbonyl)cytidine
5'-deoxy-5-ethynyl-N$^4$-[(1-isopropyl-2-methyl-propoxy)carbonyl]cytidine
5'-deoxy-5-ethynyl-N$^4$-[(3-methoxybenzyloxy)carbonyl]cytidine.

The 5'-deoxy-cytidine derivatives of formula (I) can be produced according to the following methods. In the following process A-F, P$^1$ represents a hydroxy protecting group such as acetyl, benzoyl, trimethylsilyl, tert-butyldimethylsilyl and the like.

Process A

Compounds represented by the formula (I) wherein R$^1$, R$^2$ and R$^3$ are the same as defined above can be prepared by reacting a compound represented by the formula (II)

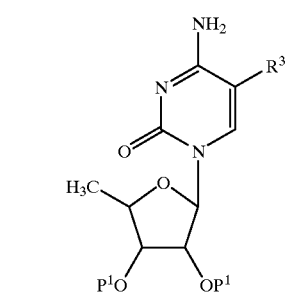

(II)

[wherein P$^1$ is a hydroxy-protecting group, and R$^3$ is the same as defined above], with a compound represented by the formula (III), $$R^4OCOX \qquad (III)$$

[wherein $R^4$ is the same as defined above; X is chloro or bromo], in the presence of acid acceptor, followed, if necessary, by removal of protecting group(s), Compounds of formula (II) can be prepared by Process D or Process E below. Compounds of formula (III) are known or can be prepared by known methods, for example, treatment of the corresponding alcohol with phosgene.

Process B

Compounds represented by the formula (I), wherein $R^1$ and $R^2$ are the same as defined above and $R^3$ is an ethynyl or vinyl group [which may be substituted with halogen atom(s), $C_{1-4}$ alkyl, cycloalkyl, aralkyl, or aromatic ring which may have one or more hetero atom(s)], can also be prepared by reacting a compound represented by the formula (IV)

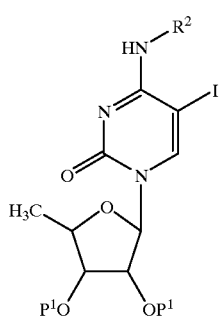

(IV)

wherein $P^1$ and $R^2$ are the same as defined above], with an acetylene or vinyl derivative in the presence of a palladium catalyst, followed, if necessary, by removal of protecting group(s).

Compounds of formula (IV) can be prepared by Process D or Process E below.

Process C

Compounds represented by the formula (I), wherein $R^1$ and $R^2$ are the same as defined above and $R^3$ is a cyano group, can be prepared by reacting a compound represented by the formula (IV)

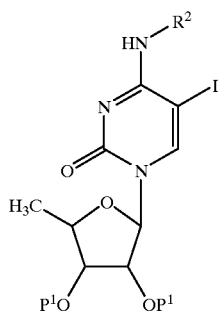

(IV)

[wherein $P^1$ and $R^2$ is the same as defined above], with alkali metal cyanide, followed, if necessary, by removal of protecting group(s).

Process D

Compounds represented by the formula (I), wherein $R^1$ and $R^3$ are the same as defined above and $R^2$ is a hydrogen atom, can also be prepared by reacting a compound represented by the formula (V)

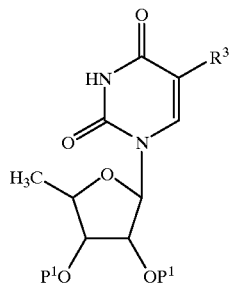

(V)

[wherein $P^1$ and $R^3$ are the same as defined above], with phosphoryl chloride in the presence of an acid acceptor, followed by treatment with ammonia, followed, if necessary, by removal of protecting group(s).

Compounds of formula V can be prepared by glycosidation reaction of a corresponding 5-substituted-uracil and protected 5-deoxyribose (VII) according to the procedure described in, for example, J. Kiss et al., Helvetica Chim. Acta., 65(5) 1522 (1982). 5-substituted-uracils can be prepared as described, for example, in J. Perman et al., Tetrahedron Letters, 28, 2427 (1976); V. Farina et al., Synlett., 157 (1991); Biochemical Pharmacology, 38,1471 (1989).

Process E

Compounds represented by the formula (I), wherein $R^1$, $R^2$ and $R^3$ are the same as defined above, can also be prepared by coupling a compound represented by the formula (VI)

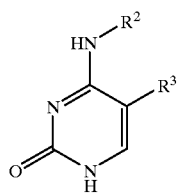

(VI)

[wherein $R^2$ and $R^3$ are the same as defined above], with a compound represented by the formula (VII)

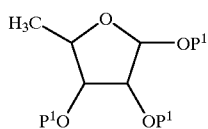

(VII)

[wherein p1 is the same as defined above] in the presence of Lewis acid catalyst, followed, if necessary, by removal of protecting group(s).

Compounds of formula VI are known [for example, A. S. Jones et al., Tetrahedron Letters, 28, 2459 (1977] or can be prepared by known methods.

Process F

Compounds represented by the formula (I) wherein $R^3$ is a vinyl radical [which may be substituted with halogen atom(s), $C_{1-4}$ alkyl, cycloalkyl, aralkyl, or aromatic ring which may have one or more hetero atom(s)], $R^1$ and $R^2$ are the same as defined above can be prepared by catalytic hydrogenation of a compound represented by the formula (VIII)

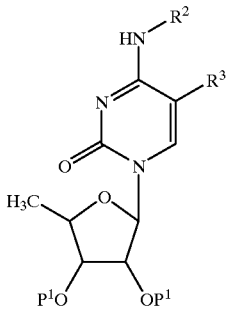

(VIII)

[wherein $P^1$ is a hydroxy-protecting radical, $R^3$ is an ethynyl radical (which may be substituted with halogen atom(s), $C_{1-4}$ alkyl, cycloalkyl, aralkyl, or aromatic ring which may have one or more hetero atom(s)), and $R^2$ is the same as defined above],
with Lindlar catalyst, followed, if necessary, by removal of protecting radical(s).

Compounds of formula (VIII) can be prepared from the compounds of formula (II) or (IV) by Process B.

In the following, process for producing 5'-deoxy-cytidine derivatives represented by the formula (I) according to the present invention will be explained in more detail.

Process A

Specific examples of the compounds represented by the formula (II) include,

2',3'-di-O-acetyl-5'-deoxy-5-ethynylcytidine,
2',3'-bis-O-(tert-butyldimethylsilyl)-5'-deoxy-5-ethynylcytidine,
2',3'-di-O-acetyl-5'-deoxy-5-prop-1-ynylcytidine,
2',3'-bis-O-(tert-butyidimethylsilyl)-5'-deoxy-5-prop-1-ynylcytidine,
2',3'-di-O-acetyl-5-but-1-ynyl-5'-deoxycytidine,
2',3'-bis-O-(tert-butyldimethylsilyl)-5-but-1-ynyl-5'-deoxycytidine,
2',3'-di-O-acetyl-5'-deoxy-5-pent-1-ynylcytidine,
2',3'-bis-O-(tert-butyidimethylsilyl)-5'-deoxy-5-pent-1-ynylcytidine,
2',3'-di-O-acetyl-5'-deoxy-5-hex-1-ynylcytidine,
2',3'-bis-O-(tert-butyidimethylsilyl)-5'-deoxy-5-hex-1-ynylcytidine,
2',3'-di-O-acetyl-5'-deoxy-5-iodocytidine,
2',3'-bis-O-(tert-butyidimethylsilyl)-5'-deoxy-5-iodocytidine,
2',3'-di-O-acetyl-5-bromo-5'-deoxycytidine,
2',3'-bis-O-(tert-butyldimethylsilyl)-5-bromo-5'-deoxycytidine,
2',3'-di-O-acetyl-5-(1-chlorovinyl)-5'-deoxycytidine,
2',3'-bis-O-(tert-butyldimethylsilyl)-5-(1-chlorovinyl)-5'-deoxycytidine,
2',3'-di-O-acetyl-5'-deoxy-5-vinylcytidine,
2',3'-bis-O-(tert-butyidimethylsilyl)-5'-deoxy-5-vinylcytidine,
2',3'-di-O-acetyl-5'-deoxy-5-trifluoromethylcytidine,
2',3'-bis-O-(tert-butyldimethylsilyl)-5'-deoxy-5-trifluoromethylcytidine,
2',3'-di-O-acetyl-5-(3-benzyloxybenzyl)-5'-deoxycytidine,
5-(3-benzyloxybenzyl)-2',3'-bis-O-(tert-butyldimethylsilyl)-5'-deoxycytidine,
2',3'-di-O-acetyl-5-cyano-5'-deoxycytidine,
2',3'-bis-O-(tert-butyidimethylsilyl)-5-cyano-5'-deoxycytidine and the like.

The reaction of the compound of the above formula (II) with the compound of the above formula (III) can be carried out in a solvent such as pyridine, dioxane, tetrahydrofuran, acetonitrile, chloroform, dichloromethane and the like in the presence of an acid acceptor such as triethylamine, pyridine, picoline, 4-(N,N-dimethylamino)pyridine, lutidine and the like. The reaction can be carried out at a temperature between 0 and 30° C.

The protecting group(s) may, if necessary, be removed after the reaction by the procedures known to those skilled in the art, e.g. by basic or acidic hydrolysis, or treatment with fluoride anion.

Process B

Specific examples of the compound represented by the formula (IV) include,

2',3'-bis-O-(tert-butyidimethylsilyl)-5'-deoxy-5-iodo-$N^4$-(methoxycarbonyl)cytidine,
2',3'-bis-O-(tert-butydimethylsily)-5'-deoxy-N4-(ethoxycarbonyl)-5-iodocytidine,
2',3'-bis-O-(tert-butyidimethylsilyl)-5'-deoxy-5-iodo-$N^4$-(n-propoxycarbonyl)-cytidine,
$N^4$-(n-butoxycarbonyl)-2',3'-bis-O-(tert-butyidimethylsilyl)-5'-deoxy-5-iodocytidine,
2',3'-bis-O-(tert-butyidimethylsilyl)-5'-deoxy-5-iodo-$N^4$-(n-pentyloxy-carbonyl)-cytidine,
2',3'-bis-O-(tert-butyidimethylsilyl)-5'-deoxy-5-iodo-$N^4$-(isopentyloxy-carbonyl)-cytidine,
2',3'-bis-O-(tert-butyidimethylsilyl)-5'-deoxy-5-iodo-$N^4$-(n-hexyloxy-carbonyl)-cytidine,
2',3'-bis-O-(tert-butyidimethylsilyl)-5'-deoxy-$N^4$-[(2-ethylbutyl)oxycarbonyl]-5-iodocytidine,
2',3'-bis-O-(tert-butyidimethylsilyl)-5'-deoxy-5-iodo-$N^4$-[(2-phenylethoxy)-carbonyl]cytidine,
2',3'-bis-O-(tert-butyidimethylsilyl)-$N^4$-[(cyclohexylmethoxy)carbonyl]-5'-deoxy-5-iodocytidine,
2',3'-bis-O-(tert-butyldimethylsilyl)-5'-deoxy-5-iodo-N4-(neopentyloxy-carbonyl)cytidine,
2',3'-bis-O-(tert-butyidimethylsilyl)-5'-deoxy-N4-[(3,3-dimethylbutoxy)-carbonyl]-5-iodocytidine,
2',3'-di-O-acetyl-5'-deoxy-5-iodo-$N^4$-(ethoxycarbonyl)-cytidine,
2',3'-di-O-acetyl-5'-deoxy-5-iodo-$N^4$-(n-propoxycarbonyl)cytidine
2',3'-di-O-acetyl-$N^4$-(n-butoxycarbonyl)-5'-deoxy-5-iodo-cytidine,
2',3'-di-O-acetyl-5'-deoxy-5-iodo-$N^4$-(n-pentyloxycarbonyl)cytidine and the like.

Specific examples of the acetylene or vinyl derivatives used for this coupling reaction are trimethysilyl acetylene, tert-butyidimethysilyl acetylene, 1-butyne, 1-pentyne, 1-heptyne, 1-hexyne, 3-methyl-1-butyne, 3,3-dimethyl-1-butyne, cyclohexylacetylene, phenylacetylene, 3-phenyl-1-propyne, tri-n-butyl(vinyl)stannane and the like.

The coupling reaction of a compound represented by the formula (IV) with an acetylene derivative can be performed in the presence of a palladium catalyst such as bis (triphenylphosphine)palladium (II) chloride-copper (I) iodide, bis(triphenylphosphine)palladium(II) acetate-copper (I) iodide and the like. The coupling reaction of a compound represented by the formula (IV) with a vinyl derivative can be performed in the presence of palladium catalyst such as tris(dibenzylideneacetone)dipalladium, tetrakis(triphenylphosphine)palladium, bis(acetonitrile)palladium (II) chloride in the presence of tri-2-furylphosphine, triphenylphosphine and the like.

These reaction can be carried out in a solvent such as chloroform, dichloromethane, tetrahydrofurane, N-methylpyrrolidone, N,N-dimethylformamide and the like. The reaction can be carried out at a temperature between 0 and 80° C., preferably between 10 and 60° C.

Process C

The reaction of the compound of the above general formula (IV) with alkali metal cyanide such as sodium cyanide, potassium cyanide etc. can be carried out in a solvent such as N,N-dimethylformamide, dimethylsulfoxide, acetonitrile and the like. The reaction can be carried out at a temperature between 0 and 100° C., preferably between 10 and 30° C.

Process D

Specific examples of the compounds represented by the formula (V) include,

2',3'-bis-O-(tert-butyldimethylsilyl)-5'-deoxy-5-ethynyluridine,

2',3'-bis-O-(tert-butyldimethylsilyl)-5'-deoxy-5-prop-1-ynyluridine,

2',3'-bis-O-(tert-butyldimethylsilyl)-5-but-1-ynyl-5'-deoxyuridine,

2',3'-bis-O-(tert-butyldimethylsilyl)-5'-deoxy-5-pent-1-ynyluridine,

2',3'-bis-O-(tert-butyidimethylsilyl)-5'-deoxy-5-hex-1-ynyluridine,

2',3'-bis-O-(tert-butyidimethylsilyl)-5'-deoxy-5-iodouridine, 5-bromo-2',3'-bis-O-(tert-butyldimethylsilyl)-5'-deoxyuridine, 2',3'-bis-O-(tert-butyidimethylsilyl)-5-(1-chlorovinyl)-5'-deoxyuridine, 2',3'-bis-O-(tert-butyldimethylsilyl)-5'-deoxy-5-vinyluridine, 2',3'-bis-O-(tert-butyidimethylsilyl)-5'-deoxy-5-trifluoromethyluridine, 5-(3-benzyloxybenzyl)-2',3'-bis-O-(tert-butyidimethylsilyl)-5'-deoxyuridine, 2',3'-bis-O-(tert-butyidimethylsilyl)-5-cyano-5'-deoxyuridine and the like.

The starting materials listed above can be prepared from the known 5-substituted uracil derivatives by the method similar to the process E wherein 5-substituted uracil derivative is used instead of 5-substituted cytosine derivative.

The reaction of the compound of the above formula (V) with phosphoryl chloride can be carried out in a solvent such as pyridine, dioxane, tetrahydrofuran, acetonitrile, chloroform, dichloromethane and the like in the presence of acid acceptor such as triethylamine, pyridine, picoline, 4-(N, N-dimethylamino)pyridine, lutidine, imidazole, N-methylimidazole, triazole and the like at a temparature between 0 and 30° C., followed by treatment with aqueous ammonia or ammonia gas in a solvent such as methanol, ethanol, acetonitrile, N,N-dimethylformamide and the like at a temperature between 0 and 30° C.

Process E

Specific examples of the compounds represented by the formula (VI) include 5-ethynylcytosine, 5-prop-1-ynylcytosine, 5-prop-1-ynylcytosine, 5-but-1-ynyl-5'-deoxycytosine, 5-pent-1-ynylcytosine, 5-hex-1-ynylcytosine, 5-iodocytosine, 5-bromocytosine, 5-(1-chlorovinyl)-cytosine, 5-vinylcytosine, 5-trifluoromethylcytosine, 5-(3-benzyloxy-benzyl)cytosine, 5-cyanocytosine, 5-ethynyl-$N^4$-(n-pentyloxycarbonyl) cytosine and the like.

Specific examples of the compound represented by the formula (VII) include known 5-deoxy-1,2,3-tri-O-acetyl-D-ribofuranoside, 5-deoxy-1,2,3-tri-O-benzoyl-D-ribofuranoside and the like.

A compound of the formula (VI) may be first converted to the trimethylsilyl derivative with silylation reagent such as hexamethyldisilazane, followed by the coupling reaction with a compound represented by the formula (VII) in the presence of Lewis acid catalyst such as tin-(IV)-chloride, titanium-(IV)-chloride and the like. This coupling reaction proceeds in a solvent such as acetonitrile, dichloromethane, chloroform, 1,2-dichloroethane, nitromethane, toluene and the like, at a temperature between 0 and 30° C., preferably between 0 and 10° C.

Process F

Specific examples of the compounds represented by the formula (VIII) include

5'-deoxy-5-ethynylcytidine,

5'-deoxy-$N^4$-(ethoxycarbonyl)-5-ethynylcytidine

5'-deoxy-5-ethynyl-$N^4$-(n-propoxycarbonyl)cytidine, $N^4$-(n-butoxycarbonyl)-5'-deoxy-5-ethynylcytidine, 5'-deoxy-5-ethynyl-$N^4$-(n-pentyloxycarbonyl)cytidine, $N^4$-(benzyloxycarbonyl)-5'-deoxy-5-ethynylcytidine, 2',3'-di-O-acetyl-5'-deoxy-5-ethynylcytidine 2',3'-di-O-acetyl-5'-deoxy-5-ethynyl-$N^4$-(ethoxycarbonyl)cytidine, 2',3'-di-O-acetyl-5'-deoxy-5-ethynyl-$N^4$-(n-propoxycarbonyl)cytidine, 2',3'-di-O-acetyl-5'-deoxy-5-ethynyl-$N^4$-(n-pentyloxycarbonyl)cytidine, 2',3'-bis-O-(tert-butyldimethylsilyl)-5'-deoxy-5-ethynylcytidine and the like.

The catalytic hydrogenation of the ethynyl group of the compound of formula (VIII) can be performed using Lindlar catalyst according to the method known to those skilled in the art [ cf. Synthetic Method, 1952, vol. 7, P38 (Interscience Publishers, Inc., New York)].

The 5'-deoxy-cytidine derivatives of the present invention can be used as antitumor agent together with known physiologically acceptable pharmaceutical carriers.

The present invention also provides a pharmaceutical composition comprising a 5'-deoxy-cytidine derivative represented by the formula (I) and 5-fluorouracil (5-FU) or a derivative thereof. With this composition, the 5'-deoxy-cytidine derivative potentiates the antitumor effect of 5-fluorouracil or its derivative by delivering a significantly higher amount of 5-FU selectively to tumor tissues without significant increase of 5-FU concentration in plasma.

For the combination of a 5'-deoxy-cytidine derivative represented by the formula (I) with 5-FU or a derivative thereof for the treatment of cancer with an improved efficacy and safety profile, the 5-FU derivative is preferably selected from the group consisting of:

5-fluoro-1-(2-tetrahydrofuryl)uracil, 1-(n-hexyloxycarbonyl)-5-fluorouracil,

5'-deoxy-5-fluorouridine,

5'-deoxy-5-fluoro-$N^4$-(n-propoxycarbonyl)cytidine, $N^4$-(n-butoxycarbonyl)-5'-deoxy-5-fluorocytidine, 5'-deoxy-5-fluoro-N⁴-(n-pentyloxycarbonyl)cytidine, 5'-deoxy-5-fluoro-N⁴-(isopentyloxycarbonyl)cytidine, 5'-deoxy-5-fluoro-N⁴-(n-hexyloxycarbonyl)cytidine, 5'-deoxy-N⁴-[(2-ethylbutyl)oxycarbonyl]-5-fluorocytidine, 5'-deoxy-5-fluoro-N⁴-[(2-phenylethoxy)carbonyl]cytidine, N⁴-[(cyclohexylmethoxy)carbonyl]-5'-deoxy-5-fluorocytidine, 5'-deoxy-5-fluoro-N⁴-(neopentyloxycarbonyl)-cytidine, 5'-deoxy-N⁴-[(3,3-dimethylbutoxy)carbonyl]-5-fluorocytidine, 5'-deoxy-5-fluoro-N⁴-(3,5-dimethylbenzoyl)cytidine, 5'-deoxy-5-fluoro-N⁴-(3,5-dichlorobenzoyl)cytidine, 2',3'-di-O-acetyl-5'-deoxy-5-fluoro-N⁴-(n-pentyloxycarbonyl)cytidine and the like.

A compound of the formula (I) can be administered either alone or simultaneously with 5-FU or a derivative thereof.

Accordingly, the pharmaceutical composition of the present invention can be obtained by formulating a compound of the formula (I) and 5-FU or a derivative thereof into a single preparation or may be provided in the form of two separate individual preparations.

A pharmaceutical composition of the formula (I) can be administered before or simultaneously with the administration of 5-FU or a derivative thereof; preferably, within 3 hour before or simultaneously with the administration of 5-FU or a derivative thereof.

In the pharmaceutical composition of the present invention comprising 5-FU or a derivative thereof and a 5'-deoxycytidine derivative represented by the general formula (I), the suitable molar ratio of two components is about 0.001–10 moles, preferably 0.002–0.5 mole of a compound of the formula (I) per mole of 5-FU or its derivative.

The present invention also provides a kit comprising a pharmaceutical composition (component A) containing a compound of the formula (I) and a pharmaceutical composition (component B) containing 5-FU or a derivative thereof.

Thus, the present invention is also concerned with pharmaceutical compositions of a compound of formula (I) and, pharmaceutical compositions with a compound of formula (1) and 5-FU or a derivative thereof, and a kit thereof for the treatment of colorectal cancer, breast cancer, stomach cancer, lung cancer, cervical cancer, bladder cancer and other malignant diseases and the like.

The pharmaceutical compositions and the components A and B of the kit of the present invention can be administered in any form, for example, tablets, pills, suppositories, capsules, granules, powders, or emulsions etc. Pharmaceutically acceptable carriers and excipients useful in formulating the pharmaceutical composition of the present invention are those commonly used. Pharmaceutically acceptable materials can be an organic or inorganic inert carrier material suitable for enteral, percutaneous or parenteral administration such as water, gelatine, gum arabic, lactose, starch, magnesium stearate, talc, vegetable oils, polyalkylene glycols and petroleum jelly. The pharmaceutical composition provided by the present invention can be administered orally, for example, in form of tablets, capsules, pills, powders, granules, solutions, syrups, suspensions or elixirs. The administration can also be carried out parenterally, for example, in form of sterile solutions, suspensions or emulsions; or locally, for example, in form of solutions, suspensions, salves, powders or aerosols. The pharmaceutical composition can be sterilized and/or can contain further adjuvants such as preserving, stabilizing setting, emulsifying agents, flavor-improving agents , salts for variation of the osmotic pressure or substances acting as buffers.

The pharmaceutical composition can be prepared in a conventional manner.

Dosage ranges for the pharmaceutical composition of the present invention depend on the route of administration, the age, weight and condition of the patient and the particular disease to be treated. In the case of oral, rectal or parenteral administration for adults, an approximate daily dosage is in the range of from about 1 mg to about 2,000 mg of a compound of formula (I) and from about 10 mg to about 4,000 mg of 5-FU or its derivative, depending on the kind of 5-FU derivative used. Oral administration is a preferred route of administration of the pharmaceutical composition according to the present invention.

The tumor selective delivery of 5-FU through the tumor DPD selective inhibition by a compound of formula (I) is evident from the test described hereafter.

1. Tumor DPD Selective Inhibition by Compound A of Example 6

The activity of compound A of Example 6 to inhibit DPD activity was compared with that of the known DPD inhibitor 5-ethynyluracil (5-EU) in BALB/c nude mice bearing the human prostate cancer xenograft PC-3. The liver and tumor tissues were resected out from each group of three mice at 2 and 8 hours after the administration of the Compound A (0.5 mmol/kg) and 5-EU (0.05 µmol/kg). DPD activity in these tissues was then measured as described elsewhere (Naguib et al., Cancer Research 45, 5405–5412, 1985). 5-EU inhibited the DPD activity both in the liver and tumor tissue, whereas compound A strongly inhibited the activity only in tumor tissue (Table 1). These results suggest that compound A of Example 6 inhibits DPD activity selectively in tumor tissue.

TABLE 1

| | Inhibition of DPD activity by Compound A of Example 6 | | | | | |
|---|---|---|---|---|---|---|
| | DPD activities (pmol/mg protein/min) | | | | | |
| | Control | | 5-EU | | Compound A | |
| Tissues | 2 hr | 8 hr | 2 hr | 8 hr | 2 hr | 8 hr |
| Liver | 288 | 162 | 46 | 83 | 177 | 326 |
| Tumor | 31 | 29 | 17 | 13 | 9 | 9 |

2. Selective increase of 5-FU levels in tumors by compound A of Example 6 in mice treated with fluoropyrimidines The experiment shown in Table 2 demonstrates that compound A of Example 6 increases 5-FU AUC (Area under curve) selectively in tumors in mice treated with fluoropyrimidines. In this study, fluoropyrimidines, such as 5-FU, doxifluridine [5'-deoxy-5-fluorouridine] and capecitabine [5'-deoxy-5-fluoro-N⁴-(n-pentyloxy-carbonyl)cytidine], were given to BALB/c nude mice bearing the human gastric cancer xenograft MKN28 in combination with either compound A or 5-EU. Then, 5-FU levels in the plasma and tumor tissues were measured at 0.25, 0.5, 2, 4 and 7 hours after each fluoropyrimidine administration (n=3 mice), and 5-FU AUC was calculated. The known DPD inhibitor 5-EU greatly increased the 5-FU AUCs both in the plasma and tumor tissues in mice treated with either 5-FU, capecitabine or doxifluridine. Since the increase of 5-FU levels in the plasma results in the systemic toxicity of 5-FU, 5-EU should enhance both the efficacy and toxicity of the fluoropyrimidines.

In contrast, compound A greatly increases the 5-FU AUCs only in tumor tissues probably as a result of compound A's tumor selective inhibition of DPD activity that catabolizes 5-FU. Compound A of Example 6 therefore enhances the efficacy of fluoropyrimidines with little increasing their toxicity.

TABLE 2

5-FU AUC in the plasma and tumors in mice treated with fluoropyrimidines

|  | Test compounds (µmol/kg) | Fluoropyrimidines (mmol/kg) | 5-FU AUC (nmol·hr/mL) Plasma | 5-FU AUC (nmol·hr/mL) Tumor |
|---|---|---|---|---|
| Exp. 1 | — | 5-FU (0.3) | 9.3 | 1.3 |
|  | Compound A (2) | 5-FU (0.3) | 9.5 | 6.0 |
|  | 5-EU (1) | 5-FU (0.3) | 75 | 48 |
|  | — | Capecitabine (1.5) | 1.3 | 30 |
|  | Compound A (2) | Capecitabine (1.5) | 3.1 | 67 |
|  | 5-EU (1) | Capecitabine (1.5) | 53 | 120 |
| Exp. 2 | — | Doxifluridine (0.75) | 2.6 | 8.0 |
|  | Compound A (2) | Doxifluridine (0.75) | 11 | 30 |
|  | 5-EU (1) | Doxifluridine (0.75) | 86 | 73 |
|  | — | Capecitabine (1.5) | 1.5 | 30 |
|  | Compound A (2) | Capecitabine (1.5) | 3.8 | 76 |
|  | 5-EU (1) | Capecitabine (1.5) | 54 | 120 |

3. Enhancement of antitumor activity of Capecitabine by Compound A of Example 6

Compound A of Example 6 was examined for its activity to enhance the efficacy of capecitabine in BALB/c nude mice bearing the human prostate cancer xenograft PC-3. Compound A and capecitabine were orally given simultaneously or sequentially 5 successive days per week for 3 weeks starting on day 53 after the tumor inoculation when the tumor becomes palpable. On day 75, tumor volume gain and the percentage of the tumor growth inhibition were calculated. As Table 3 shows, capecitabine inhibited tumor growth to a greater extent when compound A was given in combination either simultaneously or sequentially. Since compound A itself is not cytotoxic (data not shown), it enhances the efficacy of capecitabine by inhibiting DPD activity.

refluxed for 6 hr. After concentrating the reaction mixture under reduced pressure, a solution of 5-deoxy-1,2,3-tri-O-acetyl-D-ribofranoside (27.5 g, 105.8 mmol) in acetonitrile (300 ml) was added to the residue. Then, a solution of anhydrous stannic tetrachloride (27.6 g, 105.8 mmol) in nitromethane (60 ml) was added dropwise to the mixture with keeping the temperature below 0C. After stirring the mixture at 0° C. for additional 4 hr, sodium bicarbonate was added and followed by dropwise addition of water. After the mixture was stirred for 2 hr, the reaction mixture was filtered to remove insoluble material, which was washed with ethyl acetate. The filtrate and washing were combined and dried over $MgSO_4$ and filtered. The filtrate was evaporated under reduced pressure.

Purification of the residue by silica gel chromatography ( using n-hexane:ethyl acetate=1:2 as an eluent) gave 2',3'-di-O-acetyl-5'-deoxy-5-ethynyluridine (13.7 g, 48%yield ).
MALDI-MS: (m/z) 359[M+Na]$^+$, 375[M+K]$^+$,
$^1$H-NMR: (270MHz;CDCl$_3$): δ 1.47 (3H, d, J=6.6), 2.10 (3H, s), 2.12 (3H, s), 3.23 (1H, s), 4.19-4.28 (1H, m), 5.01-5.05 (1H, m), 5.30-5.34 (1H, m), 5.90 (1H, d, J=4.95), 7.57 (1H, s), 8.34 (1H, br.s)

b) Preparation of 2',3'-bis-O-(tert-butyidimethylsilyl)-5'-deoxy-5-ethynyluridine To a solution of 2',3'-di-O-acetyl-5'-deoxy-5-ethynyluridine (13.7 g, 40.7 mmol) was dissolved in methanol (100 ml) was added dropwise a solution of sodium hydroxide (3.3 g, 81.4 mmol) in water (10 ml) with stirring at 0° C. After stirring at 0° C. for additional 30 min, the reaction mixture was adjusted to pH7 with aqueous 1N-hydrochloric acid. Then the mixture was evaporated under reduced pressure.

The residue was dissolved in DMF (250 ml), and imidazole (41.6 g, 610 mM) and tert-butyidimethylchlorosilane (30.7 g, 203 mmol) was added to the solution with stirring. The mixture was continued to stir for 23 hr. The reaction mixture was partitioned between ethyl acetate and water. The aqueous layer was back-extracted with ethyl acetate. The combined organic layers were washed with brine, dried over $Na_2SO_4$, filtered and evaporated under reduced pressure. Purification of the residue by silica gel chromatography ( using n-hexane:ethyl acetate=3:1 as an eluent) gave 2',3'-bis-O-(tert-butyldimethylsilyl)-5'-deoxy-5-ethynyluridine (14.9 g, 76% yield).

TABLE 3

Enhancement of Capecitabine Efficacy by compound A of Example 6

| Capecitabine (mmol/kg/d) | Compound A (µmol/kg/d) | Tumor volume change (mm³) Day 53–75 | Tumor growth inhibition (%) Day 75 | Body weight change (g) Day 75 | Survivors on Day 75 |
|---|---|---|---|---|---|
| — | — | 981 | — | −3.6 | 5/5 |
| 1.0 | — | 757 | 23 | −3.4 | 5/5 |
| 1.0 | 1.0 | 323* | 67 | −1.8 | 5/5 |
| 1.0 | 1.0$^\#$ | 201* | 80 | −0.3 | 4/5 |

*p < 0.05 as compared with the control group
$^\#$Compound A was given one hour prior to the capecitabine administration.

The following Examples are intended to illustrate the present invention in more detail, but are not intended to limit its scope in any manner.

Reference example 1:
a) Preparation of 2',3'-di-O-acetyl-5'-deoxy-5-ethynyluridine 5-Ethynyluracil (12 g, 88.2 mmol) was suspended in a solution of ammonium sulfate (570 mg, 4.3 mmol) in hexamethyidisilazane (240 ml). The suspension was FAB-MS: (m/z) 481[M+H]$^+$,
1H-NMR: (270MHz;CDCl$_3$): δ 0.10-0.13 (12H, m), 0.91 (18H, m), 1.40 (3H, d, J=6.6), 3.21(1H, s), 3.58 (1H, dd, J=4.29, 6.6), 4.08-4.17 (2H, m), 5.62(1H, d, J=2.64), 7.68 (1H, s), 8.24(1H, br.s)

The following compounds were prepared in the same manner as described above using the corresponding known 5-substituted uracil derivatives:
2',3'-bis-O-(tert-butyidimethylsilyl)-5'-deoxy-5-iodouridine,
FAB-MS: (m/z) 583[M+H]$^+$, 605[M+Na]$^+$, ¹H-NMR: (270MHz;DMSO-d₆): δ −0.09 (3H, s), −0.03 (3H, s), 0.00 (3H, s), 0.02 (3H, s), 0.75 (9H,s), 0.81 (9H,s), 1.24 (3H, d, J=6.6), 3.75 (1H,dd, J=4.6, 4.0), 3.86 (1H, m), 4.36 (1H, dd, J=5.3, 5.0), 5.59 (I H, d, J=5.6), 7.91 (1H, s), 11.69 (1H, br.s)

2',3'-bis-O-(tert-butyldimethylsilyl)-5'-deoxy-5-trifluoromethyluridine,

FAB-MS: (m/z) 525 [M+H]⁺,

¹H-NMR: (400MHz;CDCl₃): δ 0.00 (6H, s), 0.02 (3H, s), 0.06 (3H, s), 0.83 (9H, s), 0.83 (9H, s), 1.32 (3H, d, J=5.9), 3.47 (1H, m), 4.05 (1H, m), 4.16 (1H, m), 5.54 (1H, d, J=2.2), 7.84 (1H, s), 8.43 (1H, br.s)

2',3'-bis-O-(tert-butyidimethylsilyl)-5-(3-benzyloxybenzyl)-5'-deoxy-uridine,

FAB-MS: (m/z) 653 [M+H]⁺,

¹H-NMR: (270MHz;CDCl₃): δ −0.09-0.01 (12H, m), 0.77-0.82 (18H, m), 0.90 (3H, d, J=6.3), 3.27 (1H, m), 3.31 (1H, d, J=16.5), 3.61 (1H, d, J=16.5), 3.86 (1H, m), 3.95 (1H, m), 4.94 (2H, s), 5.50 (1H, d, J=2.0), 6.68-6.78 (4H, m), 7.12-7.34 (6H, m), 8.54 (1H, br.s)

The following compounds can be prepared in the same manner as described above using the corresponding known 5-substituted uracil derivatives:

- 2',3'-bis-O-(tert-butyidimethylsilyl)-5'-deoxy-5-prop-1-ynyluridine,
- 2',3'-bis-O-(tert-butyidimethylsilyl)-5-but-I -ynyl-5'-deoxyuridine,
- 2',3'-bis-O-(tert-butyidimethylsilyl)-5'-deoxy-5-pent-1-ynyluridine,
- 2',3'-bis-O-(tert-butyidimethylsilyl)-5'-deoxy-5-hex-1-ynyluridine,
- 5-bromo-2',3'-bis-O-(tert-butyidimethylsilyl)-5'-deoxyuridine,
- 2',3'-bis-O-(tert-butyidimethylsilyl)-5-(1-chlorovinyl)-5'-deoxyuridine,
- 2',3'-bis-O-(tert-butyidimethylsilyl)-5'-deoxy-5-vinyluridine,

EXAMPLE 1

Preparation of 2',3'-bis-O-(tert-butyldimethylsilyl)-5'-deoxy-5-ethynylcytidine

To a solution of dimethylaminopyridine (19.0 g, 155.5 mmol) in acetonitrile (120 ml) and pyridine (12.6 ml, 155.5 mmol) phosphoryl chloride (14.4 g, 93.8 mM) was added dropwise in an ice bath under Ar atmosphere. After stirring the mixture for 1 hour at room temperature, a solution of 2',3'-bis-O-(tert-butyldimethylsilyl)-5'-deoxy-5-ethynyluridine (14.9 g, 31.1 mmol) in acetonitrile (80 ml) was added at 5° C. with cooling in an ice bath. The mixture was stirred at room temperature for 2 hours. Then, 25% aq. ammonia solution (10 ml) was added in one portion to the reaction mixture while keeping the temperature below 10° C. A second portion of 25% aq. ammonia solution (65 ml) was added to the reaction mixture while keeping the temperature below 10° C. The mixture was stirred at room temperature for 45 minutes. Then the reaction mixture was diluted with water (200 ml) at room temperature and extracted three times with ethyl acetate. The combined organic layers were washed successively with aq. 1N-hydrochloric acid solution, aq. saturated sodium bicarbonate and brine. The organic layer was dried over MgSO₄, filtered and evaporated under reduced pressure. Purification of the residue by silica gel chromatography (using n-hexane:ethyl acetate=2:1 as an eluent) gave 2',3'-bis-O-(tert-butyidimethylsilyl)-5'-deoxy-5-ethynylcytidine (14.8 g, 99% yield).

MALDI-MS: (m/z) 502[M+Na]⁺, 518[M+K]⁺,

¹H-NMR: (400MHz;CDCl₃): δ 0.05 (3H, s), 0.06 (3H, s), 0.12 (3H, s), 0.24 (3H, s), 0.89 (9H, s), 0.92 (9H, s), 1.41 (3H, d, J=6.35), 3.36 (1H, s), 3.46 (1H, dd, J=3.91,7.81), 4.19-4.26 (2H, m), 5.57 (1H, s), 5.79 (1H, br.s), 7.57 (1H, br.s), 7.80(1H, s)

The following compounds were obtained in a manner analogous to that of Example 1.

EXAMPLE 2

2',3'-bis-O-(tert-butyidimethylsilyl)-5'-deoxy-5-iodocytidine,

FAB-MS: (m/z) 582[M+H]⁺,

¹H-NMR: (270MHz;DMSO-d₆) δ 0.00 (3H, s), 0.02 (3H, s), 0.06 (3H, s), 0.08 (3H, s), 0.82 (9H, s), 0.88 (9H, s), 1.30 (3H, d, J=6.6), 3.78 (1H, dd, J=4.6,4.3), 3.93 (1H, m), 4.33 (1H, dd, J=4.9,4.6), 5.67 (1H, d, J=5.0), 6.67(1H, br.s), 7.87(2H, br.s)

EXAMPLE 3

2',3'-bis-O-(tert-butyidimethylsilyl)-5'-deoxy-5-trifluoromethylcytidine,

FAB-MS: (m/z) 524 [M+H]⁺,

¹H-NMR: (400MHz;CDCl3): δ 0.00 (6H, s), 0.08 (3H, s), 0.19 (3H, s), 0.84 (9H, s), 0.87 (9H, s), 1.35 (3H, d, J=6.6), 3.38 (1H, m), 4.15 (1H, m), 4.21 (1H, m), 5.51 (1H, s), 7.97 (1H, s)

EXAMPLE 4

5-(3-benzyloxybenzyl)-2',3'-bis-O-(tert-butyidimethylsilyl)-5'-deoxycytidine,

FAB-MS: (m/z) 652 [M+H]⁺,

¹H-NMR: (270MHz;CDCl₃): δ −0.01 (3H, s), 0.00 (3H, s), 0.09 (3H, s), 0.22 (3H, s), 0.86 (9H, s), 0.90 (9H, s), 1.10 (3H, d, J=6.6), 3.37 (1H, m), 3.57 (2H, s), 4.08-4.18 (2H, m), 5.03 (2H, s), 5.59 (1H, s), 6.75-6.90 (3H, m), 7.11 (1H, s), 7.26 (1H, m), 7.31-7.44 (5H, m)

EXAMPLE 5

2',3'-bis-O-(tert-butyidimethylsilyl)-5-cyano-5'-deoxycytidine

FAB-MS: (m/z) 481[M+H]⁺,

¹H-NMR: (270MHz;DMSO-d₆): δ −0.04 (3H, s), 0.00 (3H, s), 0.02 (3H,s), 0.76 (9H, s), 0.82 (9H, s), 1.21 (3H, d, J=6.3), 3.81 (1H, m), 4.05 (1H, t, J=5.0), 4.71 (1H, t, J=5.0), 5.65 (1H, d, J=5.3), 6.41 (1H, s), 7.69 (1H, br.s), 7.85 (1H, br.s)

The following compounds can be obtained according to a manner analogous to that of Example 5.

- 2',3'-bis-O-(tert-butyldimethylsilyl)-5'-deoxy-5-prop-1-ynylcytidine,
- 2',3'-bis-O-(tert-butyldimethylsilyl)-5-but-1-ynyl-5'-deoxycytidine,
- 2',3'-bis-O-(tert-butyldimethylsilyl)-5'-deoxy-5-pent-1-ynylcytidine,
- 2',3'-bis-O-(tert-butyldimethylsilyl)-5'-deoxy-5-hex-1-ynylcytidine,
- 5-bromo-2',3'-bis-O-(tert-butyidimethylsilyl)-5'-deoxycytidine,
- 2',3'-bis-O-(tert-butyldimethylsilyl)-5-(1-chlorovinyl)-5'-deoxycytidine,
- 2',3'-bis-O-(tert-butyidimethylsilyl)-5'-deoxy-5-vinylcytidine,

EXAMPLE 6

Preparation of 5'-deoxy-5-ethynyl-N$^4$-(n-pentyloxycarbonyl)cytidine, a) 2',3'-Bis-O-(tert-butyidimethylsilyl)-5'-deoxy-5-ethynylcytidine (45 mg, 0.09 mmol) was dissolved in dichloromethane (1 ml) and pyridine (33 μl, 0.42 mM). To the mixture, n-pentyl chloroformate (42 mg, 0.28 mmol) was added dropwise in an ice bath under Ar. The reaction mixture was stirred at room temperature for 2 hours. Water was added and the reaction mixture stirred for 30 minutes. The reaction mixture was partitioned between dichloromethane and water. The aqueous layer was extracted with dichloromethane. The combined organic layers were dried over Na$_2$SO$_4$ and filtered. The filtrate was evaporated under reduced pressure.

Purification of the residue by silica gel chromatography (using n-hexane:ethyl acetate=4: 1 as an eluent) gave 2',3'-bis-O-(tert-butyldimethylsilyl)-5'- deoxy-5-ethynyl-N$^4$-(n-pentyloxycarbonyl)cytidine (40 mg, 72% yield).

FAB-MS: (m/z) 594[M+H]$^+$, $^1$H-NMR: (270MHz;CDCl$_3$): δ 0.12-0.27 (12H, m), 0.90-0.92 (21H, m), 1.26-1.42 (7H, m), 1.64-1.74 (2H, m), 3.25-3.51 (2H, m), 4.15-4.23 (4H, m), 5.55-5.60 (1H, m), 7.62 (0.5H, br.s), 7.73 (0.5H, br.s), 8.00 (0.5H, br.s), 12.3 (0.5H, br.s)

b) To a solution of 2',3'-bis-O-(tert-butyidimethylsilyl)-5'-deoxy-5-ethynyl-N$^4$-(n-pentyloxycarbonyl)cytidine (19 mg, 0.03 mmol) in tetrahydrofuran (500 μl) was added dropwise tetrabutylammonium fluoride (93 μl, 0.09 mmol) [1.0M tetrahydrofuran solution] at room temperature under Ar atmosphere. After the mixture was stirred at room temperature for 2 hours, the reaction mixture was evaporated under reduced pressure. The residue was partitioned between dichloromethane and water. The aqueous layer was back-extracted with dichloromethane. The combined organic layers were dried over Na$_2$SO$_4$, filtered and evaporated under reduced pressure. Purification of the residue by silica gel chromatography (using dichloromethane: methanol=20:1 as an eluent) gave 5'-deoxy-5-ethynyl-N$^4$-(n-pentyloxycarbonyl)cytidine (compound A) (9 mg, 81% yield).

FAB-MS: (m/z) 366[M+H]$^+$, $^1$H-NMR: (400MHz;DMSO-d$_6$): δ 0.88 (3H, t, J=6.84), 1.30-1.32 (7H, m), 1.59-1.63 (2H, m), 3.67-3.71 (1H, m), 3.90-4.46 (5H, m), 5.07 (1H, m), 5.42 (1H, m), 5.66 (1H, m), 7.89 (0.5H, br.s), 8.14 (0.5H, br.s), 9.53 (0.5H, br.s), 11.7 (0.5H, br.s)

The following compounds (examples 7–41) were obtained in a manner analogous to that of Example 6.

EXAMPLE 7

5'-deoxy-5-ethyl-N$^4$-(n-pentyloxycarbonyl)cytidine

FAB-MS: (m/z) 370[M+H]$^+$, $^1$H-NMR: (270MHz;CDCl$_3$): δ 0.91(3H, t, J=6.93),1.16 (3H, t, J=7.5), 1.36 (4H, m), 1.41 (3H, d, J 6.6), 1.72 (2H, m), 2.47 (2H, q, J=7.5), 3.22 (1H, br.s), 3.93 (1H, m), 4.16 (2H, t, J=6.93), 4.28 (2H, m), 4.49 (1H, br.s), 5.66 (1H, d, J=3.63), 7.37 (1H, br.s), 12.46(1H, br.s)

EXAMPLE 8

5'-deoxy-5-iodo-N$^4$-(n-pentyloxycarbonyl)cytidine

FAB-MS: (m/z) 468 [M+H]$^+$, 490[M+Na]$^+$, $^1$H-NMR: (270 MHz; DMSO-d$_6$): δ 1.36 (3H, t, J=7.0), 1.76-1.78 (7H, m), 2.09 (2H, m), 4.18 (1H, m), 4.36 (1H, m), 4.54 (2H, t, J=5.9), 5.54 (1H, br.d, J=5.0), 5.84 (1H, br.d, J=5.0), 6.09 (1H, d, J=4.3), 8.47 (1H, s), 12.24 (1H, br.s)

EXAMPLE 9

5'-deoxy-N$^4$-(n-pentyloxycarbonyl)-5-trifluoromethylcytidine

FAB-MS: (m/z) 410[M+H]$^+$,

1H-NMR: (270MHz;CDCl$_3$): δ 0.88-0.94 (3H, m), 1.32-1.39 (4H, m), 1.42 (3H, d, J=6.6), 1.68-1.75 (2H, m), 3.09-3.30 (1H, m), 3.92 (1H, m), 4.15-4.27 (5H, m), 5.67 (1H, d, J=3.3), 8.05-8.31 (1H, m), 12.6 (1H, br.s)

EXAMPLE 10

5-(3-benzyloxybenzyl)-5'-deoxy-N$^4$-(n-pentyloxycarbonyl)cytidine

FAB-MS: (m/z) 538 [M+H]$^+$, $^1$H-NMR: (270MHz;CDCl$_3$): δ 0.90 (3H, t, J=6.9), 1.04 (3H, d, J=6.6), 1.26-1.39 (4H, m), 1.72 (2H, m), 3.16 (1H, br.s), 3.67 (1H, d, J=16.5), 3.71 (1H, m),3.75 (1H, d, J=16.5), 4.10 (2H, m), 4.16 (2H, t, J=6.9), 4.40 (1H, br.s), 5.04 (2H, s), 5.62 (1H, d, J=3.3), 6.79 (1H, d, J=7.6), 6.84-6.89 (2H, m), 6.97 (1H, br.s), 7.22-7.43 (6H, m), 12.41 (1H, br.s)

EXAMPLE 11

5-cyano-5'-deoxy-N$^4$-(n-pentyloxycarbonyl)cytidine

FAB-MS: (m/z) 367[M+H]$^+$, $^1$H-NMR: (270MHz;DMSO-d$_6$):δ 0.88 (3H, t, J=6.9),1.30 (4H, s), 1.31(3H, d, J 6.3), 1.62 (2H, m), 3.81 (1H, quin., J=6.3), 3.91 (1H, quin., J=6.3), 4.13 (2H, t, J=6.6),4.39 (1H , m), 5.09 (1H, d, J=6.3), 5.31 (1H, d, J=5.3), 5.83(1H, d, J=4.0), 7.57 (1H, s), 11.23 (1H, br.s)

EXAMPLE 12

5'-deoxy-5-ethynyl-N$^4$-(n-propoxycarbonyl)cytidine

FAB-MS: (m/z) 338[M+H]$^+$, 360[M+Na]$^+$, $^1$H-NMR: (270MHz;DMSO-d$_6$): δ 0.91 (3H, t, J=7.3), 1.31 (3H, d, J=6.3), 1.63 (2H, sextet, J=7.3), 3.69 (1H, dt, J=5.9,5.3), 3.91 (1H, quin., J=5.9), 4.03 (2H, t, J=6.6), 4.13 (1H, dt, J=5.0,4.3), 4.35 (1H, br.s), 5.05 (1H, d, J=5.9), 5.41 (1H, d, J=5.3), 5.66 (1H, d, J=4.0), 8.01 (1H, br.s)

EXAMPLE 13

5'-deoxy-5-ethynyl-N$^4$-(isopropoxycarbonyl)cytidine

FAB-MS: (m/z) 338[M+H]$^+$, $^1$H-NMR: (270MHz;DMSO-d$_6$): δ 1.24 (6H, d, J=5.9), 1.31 (3H, d, J=6.6), 3.68 (1H, dt, J=5.9,5.6), 3.90 (1H, quin., J=5.9), 4.12 (1H, m), 4.30 (1H, s), 4.85 (1H, m), 5.05 (1H, d, J=5.9), 5.40 (1H, d, J=5.3), 5.66 (1H, d, J=3.6), 8.02 (1H, br.s)

EXAMPLE 14

N$^4$-(isobutoxycarbonyl)-5'-deoxy-5-ethynylcytidine

FAB-MS: (m/z) 352[M+H]$^+$, $^1$H-NMR: (270MHz;DMSO-d$_6$): δ 0.91 (6H, d, J=6.6), 1.30 (3H, d, J=6.3), 1.91 (2H, m), 3.68 (1H, dt, J=5.9,5.3), 3.84 (2H, d, J=6.6), 3.89 (1H, quin., 6.3), 4.11 (1H, m), 4.30 (1H, s), 5.03 (1H, d, J=5.9), 5.38 (1H, d, J=5.3), 5.66 (1H, d, J=4.0), 7.96(1H, s)

EXAMPLE 15

5'-deoxy-5-ethynyl-N$^4$-[(2-methylpentyloxy)carbonyl]-cytidine

FAB-MS: (m/z) 380[M+H]$^+$, 402[M+Na]$^+$, $^1$H-NMR: (270MHz;DMSO-d$_6$): δ 0.85-0.93 (7H, m), 1.31 (3H, d, J 6.3), 1.28-1.37 (3H, m), 1.77 (1H, m), 3.69 (1H, dt, J=5.9, 5.6), 3.88(2H, m), 3.92(1H, m), 4.13 (1H, dt, J=4.9, 4.6), 4.37(1H, br.s), 5.06 (1H, d, J=5.9), 5.41 (1H, d, J=5.3), 5.66 (1H,d,J=4.0), 8.02 (1H, br.s),

EXAMPLE 16
5'-deoxy-5-ethynyl-N$^4$-[(3-methylpentyloxy)carbonyl]-cytidine

FAB-MS:(m/z) 380[M+H]$^+$, $^1$H-NMR: (270MHz;CDCl$_3$): δ 0.86-0.98 (6H, m), 1.15-1.80 (8H, m), 3.25-3.26 (1H, m), 3.53 (1H, brs), 3.90-3.95 (1H, m), 4.25-4.37 (4H, m), 5.33 (1H, brs), 5.71 (1H, d, J=4.28), 7.69 (1H, br.s), 8.13 (1H, br.s),

EXAMPLE 17
5'-deoxy-5-ethynyl-N$^4$-[(2-propylpentyloxy)carbonyl]-cytidine

MALDI-MS:(m/z) 408.5[M+H]$^+$, 430.5[M+Na]$^+$, 446 [M+K]$^+$ $^1$H-NMR: (270MHz;DMSO-d$_6$): δ 0.87 (6H, br.m), 1.29 (11H, br.m),1.66 (1H, br.m), 3.69 (1H, br.m), 3.94-4.5 (5H, br.m), 5.06 (1H, br.m), 5.42 (1H, br.m), 5.66 (1H, br.m), 7.90 (0.5H, br.s), 8.14 (0.5H, br.s), 9.53 (0.5H, br.s)

EXAMPLE 18
5'-deoxy-5-ethynyl-N$^4$-(n-octyloxycarbonyl)cytidine

FAB-MS: (m/z) 408[M+H]$^+$, 430[M+Na]$^+$, $^1$H-NMR: (270MHz;DMSO-d$_6$): δ 0.86 (3H, t, J=5.0), 1.26 (10H, m), 1.31 (3H, d, J 6.0), 1.60 (2H, m), 3.69 (1H, dt, J=5.9,5.6), 3.90 (1H, quin., J=6.3), 4.06 (2H, t, J=6.3), 4.13 (1H, m), 4.35 (1H, br.s), 5.05 (1H, d, J=5.9), 5.41 (1H, d, J=5.3), 5.66 (1H, d, J=4.0), 8.02 (1H, br.s)

EXAMPLE 19
5'-deoxy-N$^4$-[(2-ethylhexyl)oxycarbonyl]-5-ethynyl-cytidine

FAB-MS: (m/z) 408[M+H]$^+$, $^1$H-NMR: (270MHz;CDCl$_3$): δ 0.88-0.94 (6H, m), 1.30-1.41 (12H, m), 3.25 (1H, d, J=3.63), 3.53 (1H, m), 3.92-3.94 (1H, m), 4.15-4.37 (4H, m), 5.32 (1H, m), 5.70 (1H, dt, J=4.61), 7.86 (1H, br.s), 8.14 (1H, br.s)

EXAMPLE 20
5'-deoxy-5-ethynyl-N$^4$-[(2-phenylethoxy)carbonyl]-cytidine

FAB-MS: (m/z) 400[M+H]$^+$,

1H-NMR: (270MHz;DMSO-d$_6$): δ 1.31 (3H, d, J=6.3), 2.94 (2H, t, J=6.9), 3.69 (1H, dt, J=5.9,5.6), 3.90 (1H, quin., J=6.3), 4.14 (1H, m), 4.28 (2H, t, J=6.9), 4.31 (1H, br.s), 5.05 (1H, d, J=5.9), 5.41 (1H, d, J=4.9), 5.66 (1H, d, J=4.0), 7.27 (5H, m), 8.01 (1H, br.s),

EXAMPLE 21
N$^4$-(cyclohexyloxycarbonyl)-5'-deoxy-5-ethynylcytidine

FAB-MS: (m/z) 378[M+H]$^+$, $^1$H-NMR: (270MHz;DMSO-d$_6$): δ 1.06-1.48 (9H, m), 1.69 (2H, m), 1.86 (2H, m), 3.65-3.72 (1H, m), 3.88-3.93 (1H ,m), 4.13-4.61 (3H, m), 5.06 (1H, d, J=6.27), 5.42 (1H, d, J=4.95), 5.66 (1H, d, J=3.63), 7.9-8.1 (1H, m), 9.4 (0.5H, br.s), 11.8(0.5H, br.s)

EXAMPLE 22
N$^4$-[(cyclohexylmethoxy)carbonyl]-5'-deoxy-5-ethynylcytidine

FAB-MS: (m/z) 392[M+H]$^+$, 414[M+Na]$^+$, $^1$H-NMR: (270MHz;DMSO-d$_6$): δ 0.86-1.25 (5H, m), 1.31 (3H, d, J=6.3), 1.61-1.72 (6H, m), 3.69 (1H, dt, J=5.9,5.6), 3.89 (2H, d, J=6.3), 3.90 (1H, m), 4.14 (1H, m), 4.36 (1H, br.s), 5.05 (1H, d, J=5.9), 5.41 (1H, d, J=5.3), 5.66 (1H, d, J=4.0), 8.02 (1H, br.s).

EXAMPLE 23
5'-deoxy-5-ethynyl-N4-(neopentyloxycarbonyl)-cytidine

FAB-MS: (m/z) 366[M+H]$^+$, 388[M+Na]$^+$, $^1$H-NMR: (270MHz;DMSO-d$_6$): δ 0.93 (9H, s), 1.30 (3H, br.d), 3.67-4.27 (5.5H, br.m), 4.47 (0.5H, br.s), 5.06 (1H, br.m), 5.39 (1H, br.m), 5.43 (1H, br.m), 7.88 (0.5H, br.s), 8.16 (0.5H, br.s), 9.56 (0.5H, br.s), 11.69 (0.5H, br.s)

EXAMPLE 24
5'-deoxy-N4-[(3,3-dimethylbutoxy)carbonyl]-5-ethynylcytidine

FAB-MS: (m/z) 380[M+H]$^+$, $^1$H-NMR: (270MHz;DMSO-d$_6$): δ 1.01 (9H, s), 1.39 (3H, br.d), 1.63 (2H, br.t), 3.77 (1H, br.m), 3.98-4.32 (4.5H, br.m), 4.56 (0.5H, br.s), 5.13 (1H, br.m), 5.45-5.51 (1H, br.m), 5.73-5.75 (1H, br.m), 7.96 (0.5H, br.s), 8.23 (0.5H, br.s), 9.57 (0.5H, br.s), 11.76 (0.5H, br.s)

EXAMPLE 25
5'-deoxy-5-ethynyl-N4-(tridecyloxycarbonyl)cytidine

MALDI-MS: (m/z) 478[M+H]$^+$, 516[M+K]$^+$, $^1$H-NMR: (270MHz;DMSO-d$_6$): δ 0.85(3H, d, J=4.6), 1.24(20H, m), 1.30 (3H, d, J=6.3), 1.60 (2H, m), 3.68 (1H, dt, J=5.9,5.6), 3.90 (1H, quin., J =6.3), 4.05 (2H, t, J=6.6), 4.13 (1H, dt, J=5.0,4.3), 4.34 (1H, br.s), 5.05 (1H,d,J=5.9), 5.40(1H,d,J=5.3), 5.65(1H,d,J=3.6), 8.00(1H,br.s)

EXAMPLE 26
N$^4$-(n-butoxycarbonyl)-5'-deoxy-5-ethynylcytidine

FAB-MS: (m/z) 352 [M+H]$^+$, 374 [M+Na]$^+$, $^1$H-NMR: (270 MHz; DMSO-d$_6$): δ 0.89 (3H, t, J=7.2), 1.28-1.41 (5H, m), 1.53-1.64 (2H, m), 3.64 -3.71 (1H, m), 3.85-3.92 (1H, m), 4.03-4.15 (3H, m), 4.34 (1H, s), 5.04 (1H, d, J=5.9), 5.39 (1H, d, J=5.3), 5.64 (1H, d, J=3.6), 8.06 (1H, br.s)

EXAMPLE 27
5'-deoxy-5-ethynyl-N$^4$-(n-hexyloxycarbonyl)cytidine

FAB-MS: (m/z) 380 [M+H]$^+$, 402 [M+Na]$^+$, $^1$H-NMR: (270 MHz; DMSO-d$_6$): δ 0.95 (3H, t, J=6.6), 1.38-1.40 (9H, m), 1.63-1.71 (2H, m), 3.74-3.80 (1H, m), 3.94 -4.03 (1H, m), 4.14 (2H, t, J=6.6), 4.19-4.24 (1H, m), 4.43 (1H, s), 5.13 (1H, d, J=5.9), 5.49 (1H, d, J=5.3), 5.74 (1H, d, J=4.0), 8.09 (1H, br.s)

EXAMPLE 28
5'-deoxy-5-ethynyl-N$^4$-(n-decyloxycarbonyl)cytidine

FAB-MS: (m/z) 436 [M+H]$^+$, $^1$H-NMR: (270MHz; DMSO-d$_6$): d 0.85 (3H, t, J=6.4), 1.15-1.42 (17H, m), 1.60 (2H, m), 3.69 (1H, m), 3.90 (1H, m), 4.05 (2H, t, J=6.6), 4.13 (1H, m), 4.34 (1H, br.s), 5.04 (1H, d, J=5.6), 5.40 (1H, d, J=4.9), 5.66 (1H, d, J=3.6), 8.01 (1H, br.s)

EXAMPLE 29
5'-deoxy-5-ethynyl-N$^4$-[(2,6-dimethylcylohexyloxy)-carbonyl]cytidine FAB-MS: (m/z) 406 [M+H]$^+$, $^1$H-NMR: (270MHz; DMSO-d$_6$): d 0.83 (36H, d, J=6.3), 1.20-1.50 (9H, m), 1.55-1.75 (2H, m), 3.68 (1H, m), 3.93 (1H, m) 4.12-4.20 (2H, m), 4.45 (0.7H, s), 4.86 (0.3H, s), 5.04 (1H, d, J=5.6), 5.43 (1H, br.s), 5.67 (1H, br.s), 7.96 (0.3H, br.s), 8.14 (0.7H, br.s), 9.50 (0.7H, br.s) 12.00 (0.3H, br.s)

EXAMPLE 30
5'-deoxy-5-ethynyl-$N^4$-(benzyloxycarbonyl)cytidine

FAB-MS: (m/z) 386 [M+H]$^+$, $^1$H-NMR: (270MHz; DMSO-d$_6$): d 1.30 (3H, d, J=6.3), 3.69 (1H, m), 3.89 (1H, m), 4.13 (1H, m), 4.35 (1H, br.s), 5.05 (1H, d, J=5.9), 5.14 (2H, s), 5,41 (1H, d, J=5.3), 5.66 (1H, d, J=3.6), 7.31-7.45 (5H, m), 8.01 (1H, br.s)

EXAMPLE 31
5'-deoxy-5-ethynyl-$N^4$-[(1-isopropyl-2-methylpropoxy)-carbonyl]cytidine FAB-MS: (m/z) 394 [M+H]$^+$, $^1$H-NMR: (270MHz; DMSO-d$_6$): d 0.93 (12H, d, J=6.6), 1.40 (3H, d, J=6.6), 1.97 (2H, m), 3.33 (1H, d, J=3.6), 3.55 (1H, s), 3.91 (1H, m), 4.30 (1H, m), 4.36 (1H, m), 4.62 (1H, m), 5.40 (1H, s), 5.72 (1H, d, J=4.3), 7.69 (1H, s), 8.11 (1H,s)

EXAMPLE 32
5'-deoxy-5-ethynyl-$N^4$-[(3-methylbenzyloxy)-carbonyl]cytidine

FAB-MS: (m/z) 416 [M+H]$^+$, $^1$H-NMR: (270MHz; DMSO-d$_6$): d 1.31 (3H, d, J=6.0), 3.70 (1H, m), 3.76 (3H, s), 3.90 (1H, m) 4.14 (1H, m), 4.26 (0.5H, br.s), 4.44 (0.5H, br.s), 5.06 (2H, s), 5.16 (1H, br.s), 5.41 (1H, br.s), 5.66 (1H, m), 6.91 (1H, d, J=7.9), 7.00 (2H, m), 7.30 (1H, dd, J=7.9, 7.9), 7.89 (0.5H, br.s), 8.14 (0.5H, br.s), 9.72 (0.5H, br.s), 11.7 (0.5H, br.s)

EXAMPLE 33
5'-deoxy-5-ethynyl-$N^4$-(methoxycarbonyl)cytidine

FAB-MS: (m/z) 310 [M+H]$^+$, $^1$H-NMR: (270MHz; DMSO-d$_6$): d 1.30 (3H, d, J=6.3), 3.66 (3H, s), 3.70 (1H, m), 3.90 (1H, quin., J=6.3), 4.13 (1H, m), 4.34 (1H, s), 5.05 (1H, d, J=5.9), 5.40 (1H, d, J=5.3) 5.66 (1H, d, J=4.0), 8.00 (1H, br.s)

EXAMPLE 34
5'-deoxy-5-ethynyl-$N^4$-(ethyloxycarbonyl)cytidine

FAB-MS: (m/z) 324 [M+H]$^+$, $^1$H-NMR: (270MHz; DMSO-d$_6$): d 1.23 (3H, t, J=6.93), 1.31 (3H, d, J=6.27), 3.69 (1H, m), 3.90 (1H, m), 4.08-4.14 (3H, m), 4.35 (1H, br.s), 5.05 (1H, d, J=5.94), 5.40 (1H, d, J=5.27), 5.66 (1H, d, J=3.63), 8.02 (1H, br.s)

EXAMPLE 35
5'-deoxy-$N^4$-(n-pentyloxycarbonyl)cytidine

FAB-MS: (m/z) 342[M+H]$^+$, $^1$H-NMR: (270MHz;DMSO-d$_6$): δ 0.88 (3H, t, J=6.9), 1.31(4H, m), 1.32 (3H, d, J=6.3), 1.55-1.63 (2H, m), 3.63 (1H, dt, J=5.6, 5.6), 3.93 (1H, quin., J=6.3), 3.98 (1H, m), 4.01 (2H, t, J=6.9), 5.04 (1H, d, J=5.9), 5.42 (1H, d, J=4.6), 5.73 (1H, d, J=3.0), 7.07 (1H, d, J=7.6), 7.97 (1H, d, J=7.6), 10.66 (1H, br. s)

EXAMPLE 36
5'-deoxy-$N^4$-(n-pentyloxycarbonyl)-5-vinylcytidine

LC-MS: (m/z) 368 [M+H]$^+$, $^1$H-NMR: (270MHz; DMSO-d$_6$): δ 0.88 (3H, t, J=7.1), 1.31 (7H, m), 1.61 (2H, m), 3.74 (1H, m), 3.91 (1H, m), 4.06 (2H, t, J=6.4), 4.22 (1H, m), 5.08 (1H, d, J=5.3), 5.20 (1H, d, J=11.3), 5.40 (1H, d, J=4.9), 5.69 (1H, d, J=4.0), 5.88 (1H, d, J=17.9), 6.57 (1H, dd, J=11.3, 17.9), 7.78 (1H, s), 11.88 (1H, s)

EXAMPLE 37
5'-deoxy-N -(benzyloxycarbonyl)-5-vinylcytidine

FAB-MS: (m/z) 388 [M+H]$^+$, 410 [M+Na]$^+$, $^1$H-NMR: (270 MHz; DMSO-d$_6$): δ 1.30 (3H, d, J=6.3), 3.73 (1H, m), 3.92 (11H, m), 4.23 (1H, m), 5.13 (2H, s), 5.04-5.22 (2H, m), 5.42 (1H, d, J=5.3), 5.69 (1H, d, J=4.3), 5.69 (1H, dd, J=15.8, 2.0), 6.55 (1H, dd, J=11.2,15.8), 7.36-7.42 (5H, m), 7.78 (1H, s), 11.87 (1H, s).

EXAMPLE 38
N -(ethoxycarbonyl)-5'-deoxy-5-vinylcytidine

FAB-MS: (m/z) 326 [M+H]$^+$, 348 [M+Na]$^+$, $^1$H-NMR: (270 MHz; DMSO-d$_6$): δ 1.23 (3H, t, J=7.26), 1.32 (3H, d, J=6.27), 3.70-3.76 (1H, m), 3.89-3.94 (1H, m), 4.11 (2H, q, J=7.26), 4.22 (1H, m), 5.09 (1H, d, J=5.61), 5.18-5.22 (1H, m), 5.42 (1H, d, J=5.61), 5.69 (1H, d, J=3.96), 5.85-5.92 (1H, m), 6.57 (1H, dd, J=11.88,17.82), 7.79 (1H, s), 11.88 (1H, br.s)

EXAMPLE 39
5'-deoxy-5-iodo-$N^4$-[(2-phenylethoxy)carbonyl]cytidine

FAB-MS: (m/z) 502 [M+H]$^+$, $^1$H-NMR: (270MHz; DMSO-d$_6$): δ 1.30 (3H, d, J=6.3), 2.96 (2H, t, J=7.1), 3.69 (1H, m), 3.88 (1H, m), 4.17 (1H, m), 4.29 (2H, t, J=7.1), 5.07 (1H, d, J=5.9), 5.38 (1H, d, J=5.3), 5.62 (1H, d, J=4.6), 7.19-7.35 (5H, m), 8.01 (1H, s), 11.70 (1H, br.s)

EXAMPLE 40
5'-deoxy-5-iodo-$N^4$-(isopropoxycarbonyl)cytidine

MALDI-MS: (m/z) 462.5 [M+Na]$^+$, $^1$H-NMR: (270MHz; DMSO-d$_6$): δ 1.24 (6H, d, J=6.3), 1.30 (3H, d, J=6.3), 3.69 (1H, m), 3.88 (1H, m), 4.17 (1H, m), 4.87 (1H, m), 5.07 (1H, d, J=5.6), 5.38 (1H, d, J=5.3), 5.62 (1H, d, J=4.3), 8.02 (1H, s), 11.77 (1H, br.s)

EXAMPLE 41
$N^4$-(cyclohexyloxycarbonyl)-5'-deoxy-5-iodocytidine

LC-MS: (m/z) 479.9 [M+H]$^+$, $^1$H-NMR: (270MHz; DMSO-d$_6$): δ 1.23-1.42 (6H, m), 1.29 (3H, d, J=6.3), 1.70 (2H, m), 1.89 (2H, m), 3.69 (1H, m), 3.88 (1H, m), 4.16 (1H, m), 4.60 (1H, m), 5.05 (1H, d, J=5.9), 5.37 (1H, d, J=5.3), 5.62 (1H, d, J=4.3), 8.00 (1H, s)

The following compounds can also be obtained in a manner analogous to that of Example 6:

5'-deoxy-$N^4$-(n-pentyloxycarbonyl)-5-prop-1-ynylcytidine, 5-but-1-ynyl-5'-deoxy-$N^4$-(n-pentyloxycarbonyl)cytidine, 5'-deoxy-5-pent-1-ynyl-$N^4$-(n-pentyloxycarbonyl)cytidine, 5'-deoxy-5-hex-1-ynyl-$N^4$-(n-pentyloxycarbonyl)cytidine, 5'-deoxy-5-bromo-$N^4$-(n-pentyloxycarbonyl)cytidine, 5'-deoxy-5-(1-chlorovinyl)-$N^4$-(n-pentyloxycarbonyl)cytidine, 5'-deoxy-5-ethynyl-$N^4$-(isopentyloxycarbonyl)cytidine, and 5'-deoxy-$N^4$-[(2-ethylbutyl)oxycarbonyl]-5-ethynylcytidine.

EXAMPLE 42
Preparation of 2',3'-di-O-acetyl-5'-deoxy-5-iodocytidine

5-Iodocytosine (1.0 g; 4.22 mmol) and a catalytic amount of $(NH_4)_2SO_4$ were suspended in a solution of toluene (10 ml) and hexamethyidisilazane (20 ml). The suspension was heated at 110° C. for 18 hours to become a clear solution. After concentrating the reaction solution under reduced pressure, acetonitrile (25 ml) and 5-deoxy-1,2,3-tri-O-acetyl-D-ribofuranoside (1.32 g; 5.06 mmol) were added to residue. Then, anhydrous stannic chloride(0.58 ml; 5.06 mmol) in nitromethane (5 ml) was added dropwise to the mixture over 5 minutes. During the addition, the mixture was kept below 0° C. by ice cooling. After stirring the mixture at 0~5° C. for 2 hours, 2 g of sodium bicarbonate was added, followed by dropwise addition of water (0.7 ml). After the addition, the mixture was stirred vigorously at room temperature for 30 minutes. The reaction mixture was filtered to remove insoluble material, which was washed with $CH_2Cl_2$. The filtrate and washing were combined, and washed with water and sat.aq. sodium bicarbonate, and then dried over $Na_2SO_4$ and filtered. The filtrate was evaporated under reduced pressure. The crude product was purified by flash chromatography on $SiO_2$ (eluent: 5% MeOH / $CH_2Cl_2$) to give 5'-deoxy-2',3'-di-O-acetyl-5-iodocytidine as a colorless solid. (1.22 g, 66% yield)

FAB-MS:(m/z) 438[M+H]$^+$, 460[M+Na]$^+$,

1H-NMR: (270MHz;DMSO-$d_6$): δ 1.32(3H, d, J=6.3), 2.04(3H, s), 2.06(3H, s), 4.02(1H, quin., J=6.3), 5.14(1H, t, J=6.6), 5.48(1H, dd, J=6.6, 4.3), 5.69(1H, d, J=4.0), 6.78 (1H, br.s), 8.01(1H, br.s), 8.11(1H, s)

EXAMPLE 43

Preparation of 2',3'-bis-O-(tert-butyidimethylsilyl)-5'-deoxy-5-iodo-$N^4$-(n-pentyloxycarbonyl)cytidine a) 5'-deoxy-2',3'-di-O-acetyl-5-iodocytidine (200 mg; 0.46mmol) was dissolved in methanol (5 ml). To this solution 1 mol/l sodium hydoxide solution was added dropwise at 0° C. After stirring for 10 minutes, the reaction mixture was adjusted to pH 7 with 1N-hydrochloric acid solution. The reaction mixture was evaporated under reduced pressure.

A mixture of imidazole(467 mg; 6.9 mmol) in DMF(5 ml) was added to the residue. Then tert-butyidimethylchlorosilane(345 mg; 2.29 mmol) was added to the mixture. The reaction mixture was stirred at 50° C. for 1 hour. The mixture was extracted with dichloromethane, washed with water and then dried over $Na_2SO_4$ and filtered. The filtrate was evaporated under reduced pressure. The crude product was purified by flash chromatography on $SiO_2$ (eluent :70% EtOAc/n-hexane to 100% EtOAc) to give 5'-deoxy-2',3'-di-O-tert-butyldimethysilyl-5-iodocytidine as a colorless solid. (176.5 mg, 66 % yield)

FAB-MS: (m/z) 582[M+H]$^+$, $^1$H-NMR: (270MHz;DMSO-$d_6$) δ 0.00 (3H, s), 0.02 (3H, s), 0.06 (3H, s), 0.08 (3H, s), 0.82 (9H, s), 0.88 (9H, s), 1.30 (3H, d, J=6.6), 3.78 (1H, dd, J=4.6, 4.3), 3.93 (1H, m), 4.33 (1H, dd, J=4.9, 4.6), 5.67 (1H, d, J=5.0), 6.67(1H, br.s), 7.87(2H, br.s)

b) To a stirred solution of 5'-deoxy-2',3'-bis-O-(tert-butyidimethylsilyl)-5-iodocytidine (116 mg, 0.200 mmol) in $CH_2Cl_2$ (2 ml) pyridine (84 μl, 1.00 mmol), N,N-dimethylamino-pyridine (6 mg, 0.05 mmol), and n-pentyl chloroformate (95 μl, 0.600 mmol) was added at room temperature under Ar. After stirring for 30 minutes, the reaction mixture was partitioned with dichloromethane and water and the organic phase was separated and the water phase was extracted with $CH_2Cl_2$ (15 ml×4). The combined organic phase was washed with water and brine, dried over $Na_2SO_4$ and filtered. The filtrate was evaporated under reduced pressure. The crude product was purified by flash chromatography on $SiO_2$ (eluent: 20% EtOAc/n-hexane) to give 2',3'-bis-O-(tert-butyidimethylsilyl)-5'-deoxy-5-iodo-$N^4$-(n-pentyloxycarbonyl)cytidine as a colorless amorphous solid. (132.4 mg, 91 % yield)

FAB-MS: (m/z) 696 [M+H]$^+$, $^1$H-NMR: (270MHz; DMSO-$d_6$): δ 0.00 (3H, s), 0.03 (3H, s), 0.05 (3H, s), 0.07 (3H, s), 0.77 (9H, s), 0.81 (9H, s), 1.20-1.27 (10H, m), 1.46-1.55 (2H, m), 3.74 (1H, dd, J=4.6, 4.6), 3.89-4.01 (3H, m), 4.37 (1H, dd, J=4.5, 4.6), 5.55 (1H, d, J=4.6), 7.92 (1H, s), 11.70 (1H, br.s)

EXAMPLE 44

Preparation of 2',3'-bis-O-(tert-butylidimethylsilyl)-5'-deoxy-5-[(trimethylsilyl)-ethynyl]-$N^4$-(n-pentyloxycarbonyl)cytidine To a solution of 2',3'-bis-O-(tert-butyldimethylsilyl)-5'-deoxy-5-iodo-$N^4$-(n-pentyloxycarbonyl)cytidine (130 mg, 0.18 mmol) in $CH_2Cl_2$(2 ml) and $Et_3N$(2 ml) CuI (10.7 mg, 0.1056 mmol), Pd(PPh$_3$)$_2$Cl$_2$ (2.6 mg, 0.0036 mmol), and trimethylsilyl-acetylene (58.6 μl, 0.40 mmol) were added and stirred for 2 hours at room temperature under Ar in the dark. The reaction mixture was concentrated under reduced pressure and the residue was dissolved in EtOAc(25 ml×3), washed with 2% aq. EDTA.2Na(10 ml×2), water and brine, dried over $Na_2SO_4$ and filtered. The filtrate was evaporated under reduced pressure. The crude product was purified by flash chromatography on $SiO_2$ (eluent: 10% EtOAc/n-hexane) to give 2',3'-bis-O-(tert-butyidimethylsilyl)-5'-deoxy-5-[(trimethylsilyl)ethynyl]-$N^4$-(n-pentyloxycarbonyl)-cytidine as a colorless amorphous solid. (30.2 mg, 26% yield)

FAB-MS: (m/z) 666[M+H]$^+$, 688[M+Na]$^+$, $^1$H-NMR: (270MHz;DMSO-$d_6$): δ −0.18 (3H, s), -0.16 (3H, s), -0.14 (3H,s), −0.12 (3H,s), 0.00 (9H,s), 0.64 (9H, s), 0.65 (3H, s), 0.67 (9H, s), 1.01(4H, m), 1.14 (3H, d, J=6.6), 1.40 (2H, m), 3.58 (1H, t, J=4.9), 3.79 (1H, m), 3.87 (2H, m), 4.20 (1H, m), 5.43 (1H, d, J=3.6), 7.88 (1H, br.s)

EXAMPLE 45

5'-deoxy-2',3'-bis-O-(tert-butyidimethylsilyl)-5-cyanocytidine

To a stirred solution of 5'- deoxy-2', 3'-bis-(O-tert-butyidimethylsilyloxy)-5-iodocytidine (153 mg, 0.263 mmol) in DMF (5 ml) NaCN (34.3 mg, 0.70 mmol) was added at room temperature. After stirring for 1 day, the reaction mixture was concentrated under reduced pressure. The crude product was dissolved in EtOAc, and then washed with water and brine. The extract was dried over $Na_2SO_4$ and filtered. The filtrate was concentrated under reduced pressure. The crude product was purified by flash chromatography on $SiO_2$ (eluent: EtOAc) to give 5'-deoxy-2',3'-bis-O-(tert-butyldimethylsilyl)-5-cyanocytidine as a pale yellow solid. (71.1 mg, 56 % yield)

FAB-MS: (m/z) 481[M+H]$^+$,

1H-NMR: (270MHz; DMSO-$d_6$): δ −0.04 (3H, s), 0.00 (3H, s), 0.02 (3H,s), 0.76 (9H, s), 0.82 (9H, s), 1.21 (3H, d, J=6.3), 3.81 (1H, m), 4.05 (1H, t, J=5.0), 4.71 (1H, t, J=5.0), 5.65 (1H, d, J=5.3), 6.41 (1H, s), 7.69 (1H, br.s), 7.85 (1H, br.s)

EXAMPLE 46

Preparation of 2',3'-di-O-acetyl-5'-deoxy-5-vinylcytidine

To a solution of 2',3'-di-O-acetyl-5'-deoxy-5-iodocytidine (1.6 g, 3.66 mmol) in 10 ml DMF were added Pd$_2$(dba)$_3$ (67 mg, 0.073 mmol) and tri-2-furylphosphine (85 mg, 0.366 mmol) and tri-n-butyl(vinyl)stannane (2.1 ml, 7.318 mmol ) under Ar atmosphere at room temperature. After stirring for 19 hours, tri-n-butyl(vinyl)stannane (2.1 ml, 7.318 mmol ) was added to the reaction mixture, and then the reaction mixture was warmed up to 40° C. with stirring for 24 hours. The solvent was removed in vacuo, and the residue was purified on a column of silica gel (eluent: ethyl acetate ~CH₂Cl₂: MeOH=95: 5) to give 2',3'-di-O-acetyl-5'-deoxy-5-vinylcytidine (1.13 g, 92 %) as colorless solid:

FAB-MS: (m/z) 338 [M+H]⁺,

1H-NMR: ( 270MHz; DMSO-d₆): d 1.33 (3H, d, J=6.3), 2.05 (3H, s ), 2.06 (3H, s), 4.05 (1H, quin., J=6.3), 5.14 (1H, d, J=10.8), 5.16 (1H, t, J=6.6), 5.54 ( 1H, d, J=17.2 ), 5.53 ( 1H, dd, J=6.9, 5.9 ), 5.73 ( 1H, d, J=4.3 ), 6.55 (1H, dd, J=17.2, 10.8 ),7.20 (1H, br. s ),7.57 (1H, br. s ),7.88 (1H, s)

EXAMPLE 47

Preparation of 5'-deoxy-5-vinylcytidine

To a solution of 2',3'-di-O-acetyl-5'-deoxy-5-vinylcytidine (111 mg, 3.29 mmol) in 5 ml of methanol was added 1N NaOH (0.32 ml, 0.32 mmol) at room temperature. After stirring for 1 hour, 1N HCl (ca.0.3 ml) was added to the reaction mixture, and then the reaction mixture was concentrated under reduced pressure. The residue was purified by solid phase extraction (MEGA Bond Elute LRC, eluent: H₂O~H₂O: MeOH=1: 1, step gradient) to give 5'-deoxy-5-vinylcytidine (82 mg, 98%) as colorless solid:

LC-MS:(m/z) 253.9 [M+H]⁺,

¹H-NMR: ( 270MHz; DMSO-d₆ ): d 1.29 ( 3H, d, J=6.3 ), 3.68 ( 1H, m ), 3.86 (1H, m), 4.08 (1H, m), 4.97 (1H, d, J=5.9), 5.12 ( 1H, d, J=11.1 ), 5.28 (1H, d, J=5.3), 5.50 (1H, d, J=17.2 ), 5.70 ( 1H, d, J=3.6), 6.58 (1H, dd, J=11.1,17.2), 7.10 (1H, br.s), 7.42 (1H, br.s), 7.64 (1H, s)

The following examples illustrate pharmaceutical preparations containing a compound provided by the present invention.

EXAMPLE A

Interlocking gelatin capsules each containing the following ingredients were manufactured in a known manner:

| | |
|---|---|
| 5'-Deoxy-5-ethynyl-N⁴-(n-pentyloxycarbonyl)-cytidine | 40 mg |
| Lactose | 70 mg |
| Corn starch | 25 mg |
| Magnesium stearate | 1 mg |
| Crospovidone | 4 mg |
| | 140 mg |

EXAMPLE B

Interlocking gelatin capsules each containing the following ingredients were manufactured in a known manner:

| | |
|---|---|
| 5'-Deoxy-5-fluoro-N⁴-(n-pentyloxycarbonyl)-cytidine | 100 mg |
| 5'-Deoxy-5-ethynyl-N⁴-(n-pentyloxycarbonyl)-cytidine | 10 mg |
| Lactose | 70 mg |
| Corn starch | 25 mg |
| Magnesium stearate | 1 mg |
| Crospovidone | 4 mg |
| | 210 mg |

EXAMPLE C

Tablets each containing the following ingredients were manufactured in a known manner:

| | |
|---|---|
| 5'-Deoxy-5-ethynyl-N⁴-(n-pentyloxycarbonyl)-cytidine | 40 mg |
| Lactose | 70 mg |
| Magnesium stearate | 3 mg |
| Crospovidone | 7 mg |
| Povidone | 10 mg |
| | 130 mg |

If necessary, the tablet is film-coated with hydroxypropylmethyl cellulose, talc and colorant.

EXAMPLE D

Tablets each containing the following ingredients were manufactured in a known manner:

| | |
|---|---|
| 5'-Deoxy-5-fluoro-N⁴-(n-pentyloxycarbonyl)-cytidine | 300 mg |
| 5'-Deoxy-5-ethynyl-N⁴-(n-pentyloxycarbonyl)-cytidine | 20 mg |
| Lactose | 70 mg |
| Magnesium stearate | 3 mg |
| Crospovidone | 7 mg |
| Povidone | 10 mg |
| | 186 mg |

If necessary, the tablet is film-coated with hydroxypropylmethyl cellulose, talc and colorant.

What is claimed is:

1. A compound of the formula (I)

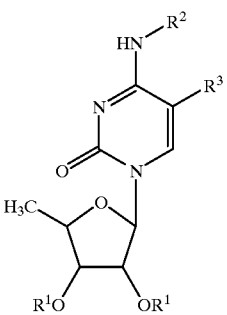

wherein $R^1$ is a hydrogen atom or a group easily hydrolyzable under physiological conditions; $R^2$ is a hydrogen atom, or —CO—OR⁴ group wherein $R^4$ is a saturated or an unsaturated, a straight or a branched hydrocarbon group consisting of one to fifteen carbon atoms, or a group of the formula —(CH₂)ₙ—Y (in which Y is cyclohexyl or phenyl; n is an integer from 0 to 4); $R^3$ is selected from the group consisting of a hydrogen atom, bromo, iodo, cyano, an unsubstituted $C_{1-4}$ alkyl group, a substituted $C_{1-4}$ alkyl group, an unsubstituted vinyl group, monosubstituted vinyl group, disubstituted vinyl group, trisubstituted vinyl group, unsubstituted ethynyl group, and a monosubstituted ethynyl group; wherein the $C_{1-4}$ alkyl substituents are one or more halo group(s); and wherein the vinyl and ethynyl substitutents are independently selected from the group consisting of a halo group, a $C_{1-4}$ alkyl, a cycloalkyl, an aralkyl, an aromatic ring, and a heteroaromatic ring with one or more heteroatoms; with the proviso that $R^2$ and $R^3$ do not simultaneously mean a hydrogen atom.

2. A compound of claim 1, wherein $R^1$ is selected from the group consisting of hydrogen, acetyl, propionyl, benzoyl, toluoyl, glycyl, alanyl, p-alanyl, valyl, and lysyl.

3. A compound of claim 2, wherein $R^1$ is hydrogen or acetyl.

4. A compound of claim 1, wherein $R^2$ is a hydrogen atom.

5. A compound of claim 1, wherein $R^2$ is a —CO—$OR^4$ group wherein $R^4$ is a saturated or an unsaturated, a straight or branched hydrocarbon group consisting of one to fifteen carbon atoms, or $R^4$ is a group of the formula —$(CH_2)_n$—Y in which Y is cyclohexyl or phenyl, and n is an integer from 0 to 4.

6. A compound of claim 5, wherein $R^2$ is a —CO—$OR^4$ group wherein $R^4$ is selected from the group consisting of methyl, ethyl, n-propyl, 1-isopropyl-2-methylpropyl, 1,1,2-trimethylpropyl, n-butyl, isobutyl, 2-ethylbutyl, 3,3-dimethyl-butyl, n-pentyl, isopentyl, neopentyl, 2-propylpentyl, n-hexyl, 2-ethylhexyl, n-heptyl, n-octyl, allyl, 2-buten-1-yl, 3-buten-1-yl, 3-penten-1-yl, 4-penten-1-yl, 3-hexen-1-yl, 4-hexen-1-yl, 5-hexen-1-yl, and n-tridecyl.

7. A compound of claim 1, wherein $R^2$ is a —CO—$OR^4$ group wherein $R^4$ is selected from the group consisting of cyclohexyl, cyclohexylmethyl, 2-cyclohexyl, 3-cyclohexylpropyl, 4-cyclohexylbutyl, phenyl, benzyl, phenethyl, 3-phenylpropyl, and 4-phenylbutyl.

8. A compound of claim 1, wherein $R^2$ is a —CO—$OR^4$ group wherein $R^4$ is selected from the group consisting of n-propyl, n-butyl, n-pentyl, isopentyl, neopentyl, n-hexyl, 3,3-dimethylbutyl, 2-ethylbutyl, phenylethyl and cyclohexylmethyl.

9. A compound of claim 1, wherein $R^3$ is selected from the group consisting of the hydrogen atom, bromo, iodo, and cyano.

10. A compound of claim 1, wherein $R^3$ is a $C_1$–$C_4$ alkyl group which is unsubstituted or substituted with one or more halogen atom(s).

11. A compound of claim 10, wherein $R^3$ is selected from the group consisting of methyl, trifluoromethyl, ethyl, and propyl.

12. A compound of claim 1, wherein $R^3$ is selected from the group consisting of an unsaturated vinyl group, a mono-substituted vinyl group, a disubstituted vinyl group, a trisubstituted vinyl group, an unsubstituted ethynyl group, and a mono-substituted ethynyl group, wherein the vinyl and ethynyl substitutents are independently selected from the group consisting of a halo group, a $C_{1-4}$ alkyl, a cycloalkyl, an aralkyl, an aromatic ring, and a heteroaromatic ring with one or more heteroatoms.

13. A compound of claim 12, wherein $R^3$ is selected from the group consisting of vinyl, 1-chlorovinyl, 2-bromovinyl, 2-bromo-1-chlorovinyl, ethynyl, prop-1-ynyl, but-1-ynyl, pent-1-ynyl, hex-1-ynyl, 3,3-dimethyl-but-1-ynyl, cyclopentylethynyl, phenylethynyl, 3-phenylprop-1-ynyl, pyrid-2-ylethynyl and imidazol-2-ylethynyl.

14. A compound of claim 1, wherein $R^3$ is selected from the group consisting of ethynyl, vinyl and iodo.

15. A compound of claim 1, 5'-deoxy-5-ethynyl-$N^4$-{(3-methoxy-benzyloxy)-carbonyl}cytidine.

16. A compound of claim 1, wherein $R^3$ is selected from the group consisting of a hydrogen atom, bromo, iodo, trifluoromethyl, ethyl, propyl, cyano, vinyl, 1-chlorovinyl, ethynyl, prop-1-ynyl, but-1-ynyl, pent-1-ynyl, hex-1-ynyl and, bromoethynyl.

17. A compound of claim 1, 5'-deoxy-5-ethynylcytidine.

18. A compound of claim 1, 5'-deoxy-5-prop-1-ynylcytidine.

19. A compound of claim 1, 5-but-1-ynyl-5'-deoxycytidine.

20. A compound of claim 1, 5'-deoxy-5-pent-1-ynylcytidine.

21. A compound of claim 1, 5'-deoxy-5-hex-1-ynylcytidine.

22. A compound of claim 1, 5'-deoxy-5-iodocytidine.

23. A compound of claim 1, 5-bromo-5'-deoxycytidine.

24. A compound of claim 1, 5-(1-chlorovinyl)-5'-deoxycytidine.

25. A compound of claim 1, 5'-deoxy-5-vinylcytidine.

26. A compound of claim 1, 5'-deoxy-5-trifluoromethylcytidine.

27. A compound of claim 1, 5-cyano-5'-deoxycytidine.

28. A compound of claim 1, 5'-deoxy-$N^4$-(n-pentyloxycarbonyl)cytidine.

29. A compound of claim 1, 5'-deoxy-$N^4$-(n-pentyloxycarbonyl)-5-prop-1-ynylcytidine.

30. A compound of claim 1, 5-but-1-ynyl-5'-deoxy-$N^4$-(n-pentyloxy-carbonyl)cytidine.

31. A compound of claim 1, 5'-deoxy-5-pent-1-ynyl-$N^4$-(n-pentyloxy-carbonyl)cytidine.

32. A compound of claim 1, 5'-deoxy-5-hex-1-ynyl-$N^4$-(n-pentyloxy-carbonyl)cytidine.

33. A compound of claim 1, 5'-deoxy-5-iodo-N4-(n-pentyloxycarbonyl)-cytidine.

34. A compound of claim 1, 5-bromo-5'-deoxy-$N^4$-(n-pentyloxy-carbonyl)cytidine.

35. A compound of claim 1, 5-(1-chlorovinyl)-5'-deoxy-$N^4$-(n-pentyloxy-carbonyl)cytidine.

36. A compound of claim 1, $N^4$-(ethoxycarbonyl)-5'-deoxy-5-vinylcytidine.

37. A compound of claim 1, 5'-deoxy-$N^4$-(n-propoxycarbonyl)-5-vinyl-cytidine.

38. A compound of claim 1, $N^4$-(n-butoxycarbonyl)-5'-deoxy-5-vinyl-cytidine.

39. A compound of claim 1, 5'-deoxy-$N^4$-(n-pentyloxycarbonyl)-5-vinyl-cytidine.

40. A compound of claim 1, $N^4$-(benzyloxycarbonyl)-5'-deoxy-5-vinyl-cytidine.

41. A compound of claim 1, 5'-deoxy-$N^4$-(n-pentyloxycarbonyl)-5-trifluoromethylcytidine.

42. A compound of claim 1, 5-cyano-5'-deoxy-$N^4$-(n-pentyloxy-carbonyl)cytidine.

43. A compound of claim 1, 5'-deoxy-5-ethynyl-$N^4$-(methoxycarbonyl)-cytidine.

44. A compound of claim 1, 5'-deoxy-$N^4$-(ethoxycarbonyl)-5-ethynyl-cytidine.

45. A compound of claim 1, 5'-deoxy-5-ethynyl-$N^4$-(n-propoxy-carbonyl)cytidine.

46. A compound of claim 1, 5'-deoxy-5-ethynyl-$N^4$-(isopropoxy-carbonyl)cytidine.

47. A compound of claim 1, $N^4$-(n-butoxycarbonyl)-5'-deoxy-5-ethynyl-cytidine.

48. A compound of claim 1, 5'-deoxy-5-ethynyl-$N^4$-(isobutoxycarbonyl)-cytidine.

49. A compound of claim 1, 5'-deoxy-5-ethynyl-$N^4$-(n-pentyloxy-carbonyl)cytidine.

50. A compound of claim 1, 5'-deoxy-5-ethynyl-$N^4$-[(2-propyl-pentyloxy)carbonyl]cytidine.

51. A compound of claim 1, 5'-deoxy-5-ethynyl-$N^4$-(isopentyloxy-carbonyl)cytidine.

52. A compound of claim 1, 5'-deoxy-5-ethynyl-$N^4$-{(2-methyl-pentyloxy)carbonyl}cytidine.

53. A compound of claim 1, 5'-deoxy-5-ethynyl-$N^4$-{(3-methyl-pentyloxy)carbonyl}cytidine.

54. A compound of claim 1, 5'-deoxy-5-ethynyl-$N^4$-(n-hexyloxy-carbonyl)cytidine.

55. A compound of claim 1, 5'-deoxy-N4-{(2-ethylbutyl)oxycarbonyl}-5-ethynylcytidine.

56. A compound of claim 1, 5'-deoxy-$N^4$-{(2-ethylhexyl)oxycarbonyl}-5-ethynylcytidine.

57. A compound of claim 1, 5'-deoxy-5-ethynyl-$N^4$-{(2-phenylethoxy)-carbonyl}cytidine.

58. A compound of claim 1, $N^4$-(cyclohexyloxycarbonyl)-5'-deoxy-5-ethynylcytidine.

59. A compound of claim 1, $N^4$-{(cyclohexylmethoxy)carbonyl}-5'-deoxy-5-ethynylcytidine.

60. A compound of claim 1, 5'-deoxy-5-ethynyl-$N^4$-(neopentyloxy-carbonyl)cytidine.

61. A compound of claim 1, 5'-deoxy-$N^4$-{(3,3-dimethylbutoxy)carbonyl}-5-ethynylcytidine.

62. A compound of claim 1, 2',3'-di-O-acetyl-5'-deoxy-5-ethynyl-$N^4$-(n-propoxycarbonyl)cytidine.

63. A compound of claim 1, 2',3'-di-O-acetyl-5'-deoxy-5-ethynyl-$N^4$-(n-pentyloxycarbonyl)-cytidine.

64. A compound of claim 1, 2',3'-di-O-acetyl-5'-deoxy-5-vinylcytidine.

65. A compound of claim 1, 2',3'-di-O-acetyl-$N^4$-(ethoxycarbonyl)-5'-deoxy-5-vinylcytidine.

66. A compound of claim 1, 2',3'-di-O-acetyl-5'-deoxy-$N^4$-(n-propoxy-carbonyl)-5-vinylcytidine.

67. A compound of claim 1, 2',3'-di-O-acetyl-$N^4$-(n-butoxycarbonyl)-5'-deoxy-5-vinylcytidine.

68. A compound of claim 1, 2',3'-di-O-acetyl-5'-deoxy-$N^4$-(n-pentyloxy-carbonyl)-5-vinylcytidine.

69. A compound of claim 1, 2',3'-di-O-acetyl-$N^4$-(benzyloxycarbonyl)-5'-deoxy-5-vinylcytidine.

70. A compound of claim 1, 5'-deoxy-5-ethynyl-$N^4$-(n-decyloxy-carbonyl)cytidine.

71. A compound of claim 1, 5'-deoxy-5-ethynyl-$N^4$-{(2,6-dimethylcyclo-hexyloxy)-carbonyl}cytidine.

72. A compound of claim 1, 5'-deoxy-5-ethynyl-$N^4$-(benzyloxy-carbonyl)cytidine.

73. A compound of claim 1, 5'-deoxy-5-ethynyl-$N^4$-{(1-isopropyl-2-methyl-propoxy)carbonyl}cytidine.

* * * * *

UNITED STATES PATENT AND TRADEMARK OFFICE
CERTIFICATE OF CORRECTION

PATENT NO. : 6,114,520
DATED : September 5, 2000
INVENTOR(S) : Hattori, et al.

It is certified that error appears in the above-identified patent and that said Letters Patent is hereby corrected as shown below:

IN THE CLAIMS:

Claim 2, Column 27, line 3: "p-alanyl" should read --- β-alanyl --- .

Signed and Sealed this

Twenty-fourth Day of April, 2001

Attest:

NICHOLAS P. GODICI

Attesting Officer    Acting Director of the United States Patent and Trademark Office